US010086128B2

(12) United States Patent
Kyle et al.

(10) Patent No.: US 10,086,128 B2
(45) Date of Patent: Oct. 2, 2018

(54) FLUID CONCENTRATOR, AUTOLOGOUS CONCENTRATED BODY FLUIDS, AND USES THEREOF

(71) Applicant: SpineSmith Holdings, LLC, Austin, TX (US)

(72) Inventors: Matthew R. Kyle, Plymouth, MN (US); Thomas Coull, Rancho Palos Verdes, CA (US)

(73) Assignee: SpineSmith Holdings, LLC, Austin, TX (US)

( * ) Notice: Subject to any disclaimer, the term of this patent is extended or adjusted under 35 U.S.C. 154(b) by 0 days.

(21) Appl. No.: 14/322,735

(22) Filed: Jul. 2, 2014

(65) Prior Publication Data

US 2015/0157781 A1 Jun. 11, 2015

Related U.S. Application Data

(63) Continuation of application No. 12/666,131, filed as application No. PCT/US2008/067677 on Jun. 20, 2008, now abandoned.

(60) Provisional application No. 60/945,733, filed on Jun. 22, 2007.

(51) Int. Cl.
| | |
|---|---|
| *A61M 1/34* | (2006.01) |
| *B01D 21/26* | (2006.01) |
| *A61M 1/36* | (2006.01) |
| *A61K 35/14* | (2015.01) |
| *A61K 35/16* | (2015.01) |
| *A61K 35/28* | (2015.01) |
| *A61K 35/30* | (2015.01) |
| *A61K 35/32* | (2015.01) |
| *A61K 35/38* | (2015.01) |
| *A61K 35/50* | (2015.01) |
| *A61K 35/52* | (2015.01) |
| *B01D 21/00* | (2006.01) |
| *B01D 63/02* | (2006.01) |
| *B01D 65/00* | (2006.01) |
| *B04B 1/00* | (2006.01) |
| *B04B 5/04* | (2006.01) |
| *B01D 21/34* | (2006.01) |
| *B01D 15/38* | (2006.01) |
| *B01D 24/00* | (2006.01) |
| *B01D 24/10* | (2006.01) |
| *B01D 61/24* | (2006.01) |
| *A61M 1/26* | (2006.01) |

(52) U.S. Cl.
CPC .......... *A61M 1/3633* (2013.01); *A61K 35/14* (2013.01); *A61K 35/16* (2013.01); *A61K 35/28* (2013.01); *A61K 35/30* (2013.01); *A61K 35/32* (2013.01); *A61K 35/38* (2013.01); *A61K 35/50* (2013.01); *A61K 35/52* (2013.01); *A61M 1/262* (2014.02); *A61M 1/34* (2013.01); *A61M 1/3693* (2013.01); *A61M 1/3696* (2014.02); *B01D 15/3809* (2013.01); *B01D 15/3828* (2013.01); *B01D 21/0012* (2013.01); *B01D 21/262* (2013.01); *B01D 21/34* (2013.01); *B01D 24/007* (2013.01); *B01D 24/10* (2013.01); *B01D 61/246* (2013.01); *B01D 63/02* (2013.01); *B01D 65/00* (2013.01); *B04B 1/00* (2013.01); *B04B 5/04* (2013.01); *A61M 2202/0405* (2013.01); *A61M 2202/0413* (2013.01); *A61M 2202/0415* (2013.01); *A61M 2202/0464* (2013.01); *A61M 2202/0466* (2013.01); *A61M 2202/0496* (2013.01); *A61M 2202/07* (2013.01); *A61M 2202/09* (2013.01); *A61M 2202/10* (2013.01); *A61M 2205/3306* (2013.01); *A61M 2205/3331* (2013.01); *A61M 2205/75* (2013.01); *B01D 2221/10* (2013.01); *B01D 2313/10* (2013.01); *B01D 2313/243* (2013.01); *B01D 2313/50* (2013.01); *B01D 2313/90* (2013.01); *B04B 2005/0478* (2013.01)

(58) Field of Classification Search
None
See application file for complete search history.

(56) References Cited

U.S. PATENT DOCUMENTS

| | | | | |
|---|---|---|---|---|
| 5,167,812 | A * | 12/1992 | Graves ............... | B01D 15/1807 210/198.2 |
| 2003/0127393 | A1* | 7/2003 | Tepper ................. | A61L 2/0017 210/656 |
| 2005/0009000 | A1* | 1/2005 | Wilhelm .................. | A01N 1/00 435/1.1 |
| 2005/0095695 | A1* | 5/2005 | Shindler et al. ........... | 435/285.1 |
| 2005/0184012 | A1* | 8/2005 | Coull et al. .................. | 210/787 |

(Continued)

OTHER PUBLICATIONS

Pitney et al. Retention of platelets by glass bead filters. 1967. J. Clin. Path. vol. 20, pp. 710-716.*

*Primary Examiner* — Channing S Mahatan
(74) *Attorney, Agent, or Firm* — Winstead PC

(57) ABSTRACT

The present invention provides devices and methods for concentrating a fluid and for treating a patient with the concentrated fluid. The concentrator apparatus includes a main housing (12) defining a separation chamber (14), a filter housing (48) containing a filter (46) comprising a filter element, a piping (44) for moving concentrated fluid from the separation chamber to the filter, and ports (32) for pressurizing the concentrated fluid past the filter element of the filter. The present invention also provides a variety of uses of concentrated body fluids, including autologous concentrated body fluid. The concentrated fluids can be used for example in surgical applications, including graft applications such as allograft, xenograft and autograft applications.

17 Claims, 8 Drawing Sheets

(56) References Cited

U.S. PATENT DOCUMENTS

2005/0260175 A1* 11/2005 Hedrick ................ A61B 17/00
424/93.7

* cited by examiner

FLUID CONCENTRATOR, AUTOLOGOUS CONCENTRATED BODY FLUIDS, AND USES THEREOF

CROSS REFERENCE TO RELATED APPLICATIONS

This application is a continuation of U.S. application Ser. No. 12/666,131, filed on 28 Jun. 2010, which is a National Stage Application of PCT/US2008/067677, filed on 20 Jun. 2008, which claims the benefit of U.S. Provisional Patent Application Ser. No. 60/945,733 filed on 22 Jun. 2007, and which applications are incorporated herein by reference. To the extent appropriate, a claim of priority is made to each of the above disclosed applications.

BACKGROUND

The present invention is directed to devices and methods for concentrating fluids. More particularly, the present invention is directed to devices and methods for concentrating autologous biological or body fluids.

Concentration and/or filtration of body fluids have long been practiced in the medical arts. Many medical treatments involve applying a fluid or gel-like substance to a wound or disease location. For some medical treatments, the fluid or gel-like substance is obtained from a body fluid of another person or animal. Body fluids, components of body fluids, or components of other body parts, such as tissue, may also be obtained from other species and used on human patients. Examples of such biological materials which are commonly used in current medical applications on humans are components of mammalian blood and bone, such as allogenic, xenogenic or autogenic graft materials, including from human, bovine and porcine sources. In some applications, the filtration and/or concentration process is carried out in an ongoing, streaming process, wherein the body fluid is simultaneously removed from the patient's body and then downstream returned to the patient's body. In other applications, the filtration and/or concentration process is carried out in a batch process, wherein an amount of the body fluid is removed from the body as a unit, treated, and then returned to the patient's body as a unit.

More recently, body fluids such as blood fractions separated by centrifugation have been further filtered to increase cell or component concentrations in the filtrate. U.S. Pat. Nos. 5,733,545; 6,010,627; and 6,342,157 show examples of this, and are incorporated by reference. Such concentrated, centrifuged body fluids have been shown to be useful in various treatment modalities, such as applying the concentrated blood component directed to an orthopedic wound site. However, the methods and devices taught in the above patents have shortcomings which have prevented widespread acceptance and use in an operating environment. For example, the fluid or gel-like substance obtained from a body fluid of another person or animal is used in treatment and when applied to a patient, increases the risk for infection or diseases such as hepatitis or AIDS. The use of autologous body fluids avoids the risk of contracting a disease from external body fluids. When body fluids or components of body fluids are obtained from other species for use in human treatment, adverse reactions such as allergies, rejection, etc. can occur. The use of autologous body fluids also avoids the risk of rejection and other adverse reactions to fluids or tissue from an outside source.

Therefore, there is a need for devices and methods for concentrating and/or filtering body fluids or autologous fluids in an efficient manner that prevents contamination of the fluids and allows the fluids to be used in treatment procedures where the risk of contamination, infection, or rejection remains high.

SUMMARY

In an aspect, the present invention includes an apparatus and method for concentrating a fluid, particularly an autologous fluid, for treatment of a patient. The concentrator apparatus includes a main housing defining a gravitational separation chamber, a filter housing containing a filter comprising a filter element, a piping for moving concentrated fluid from the separation chamber to the filter housing, and ports for pressurizing the concentrated fluid past the filter element of the filter. In an embodiment, the gravitational separation chamber is a centrifuge chamber.

In another aspect, the present invention involves the creation and use of concentrated body fluids. A body fluid or tissue is extracted from a patient. The extracted substance is separated into different gravitational fractions, such as by centrifuge separation, gravitational weight separation or by mixing the extracted substance with a reagent that causes separation and/or precipitation. Once separated into different fractions, a portion of the column height is extracted, and then passed through a filter. The resultant concentrated, filtered product is then applied to a particular location with the same patient who provided the initial body fluid or tissue, or in a different patient. Depending upon which fraction is concentrated and filtered from which body fluid, the present invention can be used to treat a variety of conditions.

In a third aspect, the concentrated autologous fluids are used in graft applications, including allograft, xenograft and autograft applications. The concentrated autologous fluids can be used to reconstitute freeze-dried or powdered allograft, autograft or xenograft materials. The concentrated fluids may also be applied directly to allografts or autografts during implantation, growth factors in the concentrated fluid promoting healing and tissue regeneration after implant surgery. The concentrated fluids may be coated onto an allograft material that then binds and/or interacts with reactive functional groups coated onto a polymer core, allowing the allograft to release growth factors in a controlled manner over the period of time required for healing after surgery.

Figure 1:
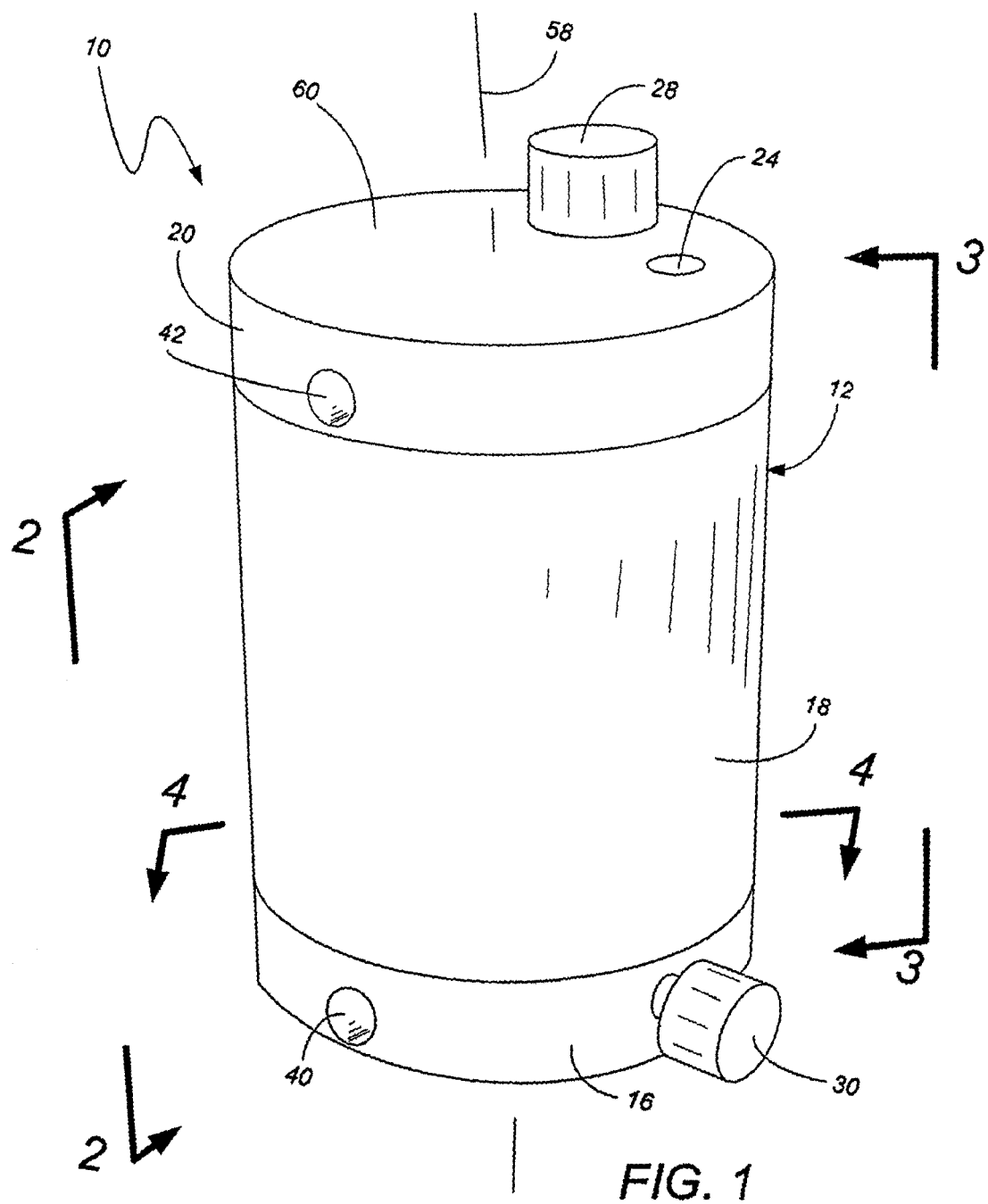
FIG. 1 is a perspective view of a first embodiment of the invention.

While the above-identified drawing figures set forth preferred embodiments, other embodiments of the present invention are also contemplated, some of which are noted in the discussion. In all cases, this disclosure presents the illustrated embodiments of the present invention by way of representation and not limitation. Numerous other minor modifications and embodiments can be devised by those skilled in the art which fall within the scope and spirit of the principles of this invention.

DETAILED DESCRIPTION

Various embodiments of the present invention will be described in detail with reference to the drawings, wherein like reference numerals represent like parts throughout the several views. Reference to various embodiments does not limit the scope of the invention, which is limited only by the scope of the claims attached hereto. Additionally, any examples set forth in this specification are not intended to be limiting and merely set forth some of the many possible embodiments for the claimed invention.

Definitions

Unless defined otherwise, all technical and scientific terms used herein have the same meaning as commonly understood to one of ordinary skill in the art. Although any methods, devices and material similar or equivalent to those described herein can be used in practice or testing, the methods, devices and materials are now described.

The term "body fluid" refers to a biological fluid collected from a subject. The subject can be a mammal, including but not limited to human, bovine, pig, sheep, horse, or goat. The body fluids can be autologous. Body fluids include, but are not limited to, blood, plasma, serum, urine, saliva, mucus, cerebrospinal fluid, lymphatic fluid, seminal fluid, amniotic fluid, vitreous fluid, as well as fluid collected from cell culture of patient cells, and the like. Body fluids also include tissue such as, for example, bone, bone marrow, muscle tissue, brain, heart, liver, lung, stomach, small intestine, large intestine, colon, uterus ovary, testis, cartilage, soft tissue, skin, subcutaneous tissue, breast tissue, tissue obtained from other species, patient tissue from surgery, and the like. The tissue can be disrupted. Methods for disrupting tissue are known and include homogenization and enzymatic treatments. The body fluids of the invention also include, for example, bone marrow, fluids obtained from surgery, fluid filtrates, tissue filtrates or fragments, bone chips or fragments obtained during surgery, and the like.

The term "concentrated" refers to a fluid which has been separated by gravity, centrifugation, and/or filtration into various fractions. The term fraction refers to the various components into which a biological fluid can be separated by centrifugation, gravitational weight separation and/or filtration. Each fraction is richer in a particular fluid component (i.e. concentrated) relative to the other fraction and the original fluid. The concentration process also removes nonessential components such that the concentrated fraction contains only necessary or desired components.

"Allograft" as used herein refers to a tissue or organ obtained from one patient and grafted to a genetically dissimilar patient. When the tissue or organ is obtained from one part of the patient's body and is grafted to another part of the same patient's body, the material is an autograft. Allograft materials include, without limitation, bone, bone powder, bone chips, or bone particles, tendons, ligaments, skin, lens fragments, and the like, obtained from mammalian sources, including bovine, porcine and human sources. Human sources include patients and cadavers. Allograft materials are usually freeze-dried and must be reconstituted in a biocompatible fluid prior to use. Allograft materials may also be substituted with biosynthetic and synthetic materials including, without limitation, demineralized bone matrix, collagen, ceramics, cements, polymers and copolymers.

The term "growth factor" as used herein means a bioactive molecule that promotes proliferation of a cell or tissue. Growth factors useful in the present invention include, but are not limited to, transforming growth factor-alpha (TGF-alpha), transforming growth factor-beta (TGF-beta), platelet-derived growth factors including the AA, AB and BB isoforms (PDGF), fibroblast growth factors (FGF), including FGF acidic isoforms 1 and 2, FGF basic form 2, and FGF 4, 8, 9 and 10, nerve growth factors (NGF) including NGF 2.5s, NGF 7.0s and beta NGF and neurotrophins, brain derived neurotrophic factor, cartilage derived factor, bone growth factors (BGF), basic fibroblast growth factor, insulin-like growth factor (IGF), vascular endothelial growth factor (VEGF), EG-VEGF, VEGF-related protein, Bv8, VEGF-E, granulocyte colony stimulating factor (G-CSF), insulin like growth factor (IGF) I and II, hepatocyte growth factor, glial neurotrophic growth factor (GDNF), stem cell factor (SCF), keratinocyte growth factor (KGF), transforming growth factors (TGF), including TGFs alpha, beta, beta1, beta2, and beta3, skeletal growth factor, bone matrix derived growth factors, and bone derived growth factors and mixtures thereof. Some growth factors can also promote differentiation of a cell or tissue. TGF and VEGF, for example, can promote growth and/or differentiation of a cell or tissue. Some preferred growth factors include VEGF, NGFs, PDGF-AA, PDGF-BB, PDGF-AB, FGFb, FGFa, and BGF.

The term "differentiation factor" as used herein means a bioactive molecule that promotes differentiation of cells or tissue. The term includes, but is not limited to, neurotrophin, colony stimulating factor (CSF), or transforming growth factor. CSF includes granulocyte-CSF, macrophage-CSF, granulocyte-macrophage-CSF, erythropoietin, and IL-3. Some differentiation factors can also promote growth or proliferation of a cell or tissue. TGF and IL-3, for example, can promote differentiation and/or growth of cells.

"Chemotactic factors" refers to a bioactive molecule responsible for regulating the movement of essential chemicals necessary for proper development, healing and/or homeostasis of cells and tissues. Chemotactic factors include cytokines. Cytokines include, but are not limited to, cardiotrophin, stromal cell derived factor, macrophage derived chemokine (MDC), melanoma growth stimulatory activity (MGSA), macrophage inflammatory proteins 1 alpha (MIP-1 alpha), 2, 3 alpha, 3 beta, 4 and 5, interleukin (IL) 1, IL-2, IL-3, IL-4, IL-5, IL-6, IL-7, IL-8, IL-9, IL-10, IL-11, IL-12, IL-13, TNF-alpha, and TNF-beta.

The term "adhesion molecule" refers to bioactive molecules that promote or facilitate adhesion with other cells or with the extracellular matrix (ECM) or basement membrane (BM). Adhesive proteins include actin, fibrin, fibrinogen, fibronectin, vitronectin, laminin, cadherins, selectins, intracellular adhesion molecules 1, 2, and 3, and cell-matrix adhesion receptors including but not limited to integrins such as $\alpha_5\beta_1$, $\alpha_6\beta_1$, $\alpha_7\beta_1$, $\alpha_1\beta_2$, $\alpha_2\beta_3$, and $\alpha_6\beta_4$.

As used herein, the terms "treatment" and "treating" refer to the process of administering or applying a concentrated biological fluid or concentrated body fluid to a patient at the site of a wound or injury in order to cause or promote healing at the wound or injury site. The concentrated fluid can be autologous. The concentrated fluid or concentrated body fluid is applied in a therapeutically effective amount. For example, an amount sufficient to cause wound or injury healing when an autologous fluid is applied to a wound or injury site would be a therapeutically effective amount.

MODES FOR CARRYING OUT THE INVENTION

The present invention is directed to concentration of body fluids using a concentrator device, and uses of concentrated body fluids and similar substances produced using the concentrator device. Concentrated body fluids obtained by the methods of the present invention having many uses, including treatment of a variety of medical conditions.

A. Fluid Concentrator

The present invention includes a fluid concentrator device for concentrating body fluids. The body fluids can be autologous body fluids. The concentrator 10 of the present invention primarily includes a main housing 12 which defines separation chamber 14. For ease of manufacture and assembly, the main housing 12 may be formed as a base plate 16, a central housing 18, and a top plate 20 as shown in FIG. 1. The main housing 12 is preferably molded of plastic, but could be formed of any sterilizable material. As part of manufacture and assembly, the base plate 16, central housing 18 and top plate 20 are preferably sealed to each other, such as through an epoxy sealant or sonic welding. The base plate 16, central housing 18 and top plate 20 may alternatively be formed with mating threads so as to screw together, and sealed such as with a common O-ring.

An embodiment, the central housing 18 is transparent or semi-transparent, thereby allowing viewing of the fluid contained within the centrifugation chamber 14 of the central housing 18. This allows viewing of the body fluid after separation, to better determine which fraction of the fluid to remove from the separation chamber 14. Alternatively, the central housing 18 may include a window, i.e., a portion which is transparent or semi-transparent. When a biological fluid or body fluid is placed into the chamber 14 and centrifuged, color distinctions between the various components or fractions can be visually discerned. For example, where the body fluid is blood, platelet poor plasma, buffy coat and red blood cell fractions or components have distinct colors and can be visually distinguished from one another. For fluids which do not visually separate during centrifugation or gravitational separation weight, or if a float or other mechanism is used to determine which portion of the separated fluid to remove from the separation chamber 14, no window is necessary.

In an embodiment, the overall size of the main housing 12 is selected to be compatible with existing centrifuges. For example, centrifuges are presently available which handle 4×4 inch vessels, and the main housing 12 is dimensioned to mate with and be received by the common 4×4 inch centrifuge (not shown). In an embodiment, the main housing 12 is dimensioned to mate with and be received by a 8×8 inch centrifuge. In an embodiment, the main housing 12 is dimensioned to mate with and be received by a 12×12 inch centrifuge. In an embodiment, the main housing 12 is dimensioned to mate with and be received by up to a 40×40 inch centrifuge, such as for small volumes up to 250 µL. The bottom wall 22 of the base plate 16 is flat and includes no ports or items projecting from it, so the concentrator 10 can stand on a flat surface and will be stable during centrifugation.

The top plate 20 includes an opening 24 which serves as a fluid inlet. The inlet 24 preferably includes a closure mechanism 26 (shown schematically in FIG. 3). The closure mechanism 26 could be a rubber stopper, with the fluid hypodermically injected through the rubber stopper into the separation chamber 14. However, the preferred closure mechanism 26 is a cap with a hand-turnable luer lock, commonly known in the fluid handling art.

Figure 2:
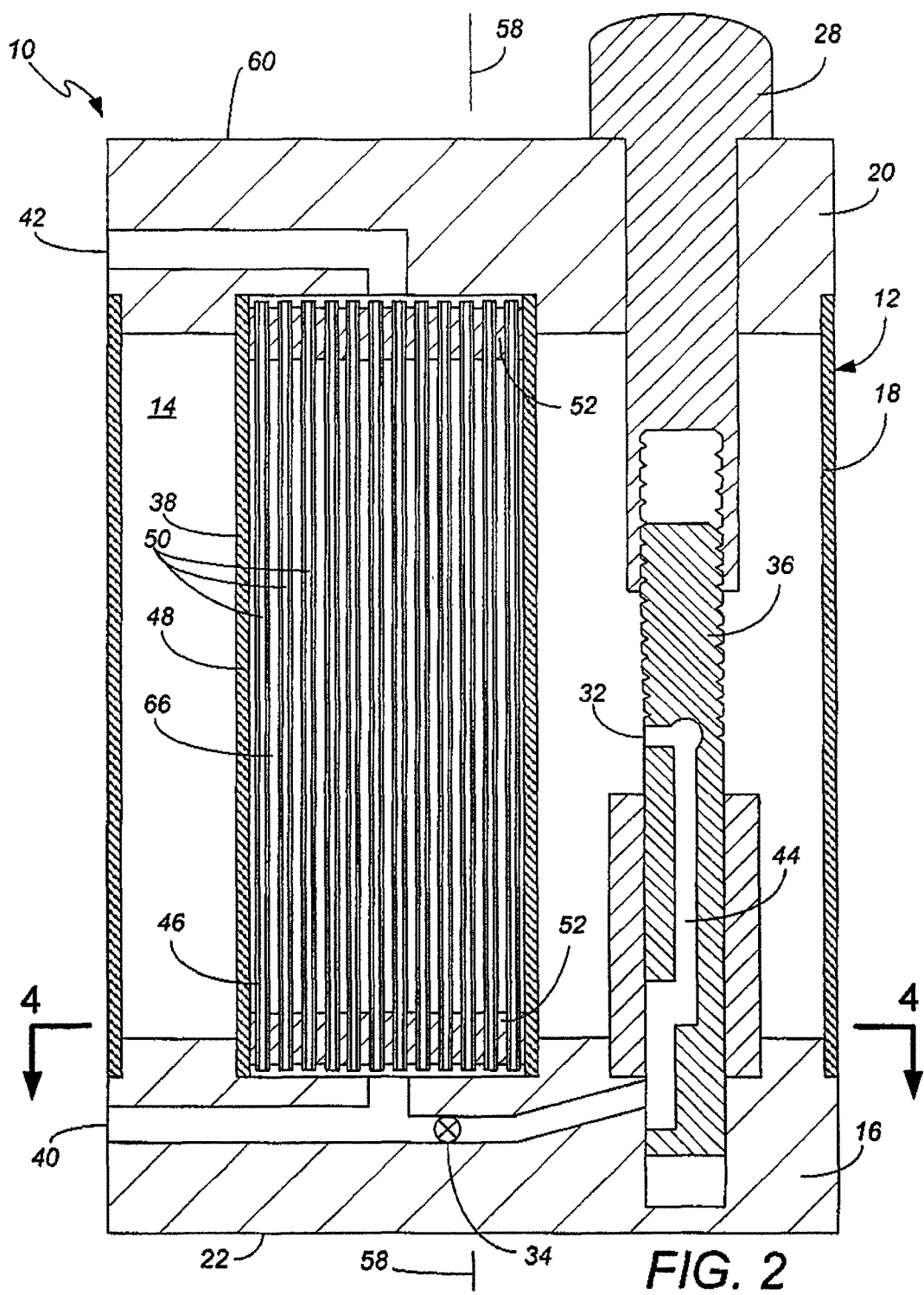
FIG. 2 is a cross-sectional side view of the embodiment of FIG. 1 taken along lines 2-2.

As shown in FIG. 1, a valve adjustment handle 28 is accessible in the top plate 20, and a valve control handle 30 is accessible in the base plate 16. These two handles 28, 30 control a valve inlet 32 and valve 34 (shown in FIG. 2) which are located within the concentrator 10. The valve adjustment handle 28 allows hand rotation of a threaded valve opening stem 36, the rotation of which changes the height of the valve inlet 32 relative to the main housing 12. As best shown in FIG. 2, the valve adjustment handle 28 is used to position the valve inlet 32 at a desired height to correspond with the height of the desired fluid layer after separation. The valve inlet 32 thus serves as the outlet port to remove a fraction of fluid from the separation chamber 14. While a threaded stem 36 provides an easy way of adjusting the height of the valve inlet 32, many equivalent mechanisms could be used such as a slide, float or other adjustment feature.

As shown in FIG. 2, a filter unit 38 is disposed within the separation chamber 14. The filter unit 38 connects between a base port 40 defined in the base plate 16 and a top port 42 defined in the top plate 20. Piping 44 is included to transport the fluid from the valve inlet 32 to the base port 40 or inlet to the filter unit 38.

Figure 3:
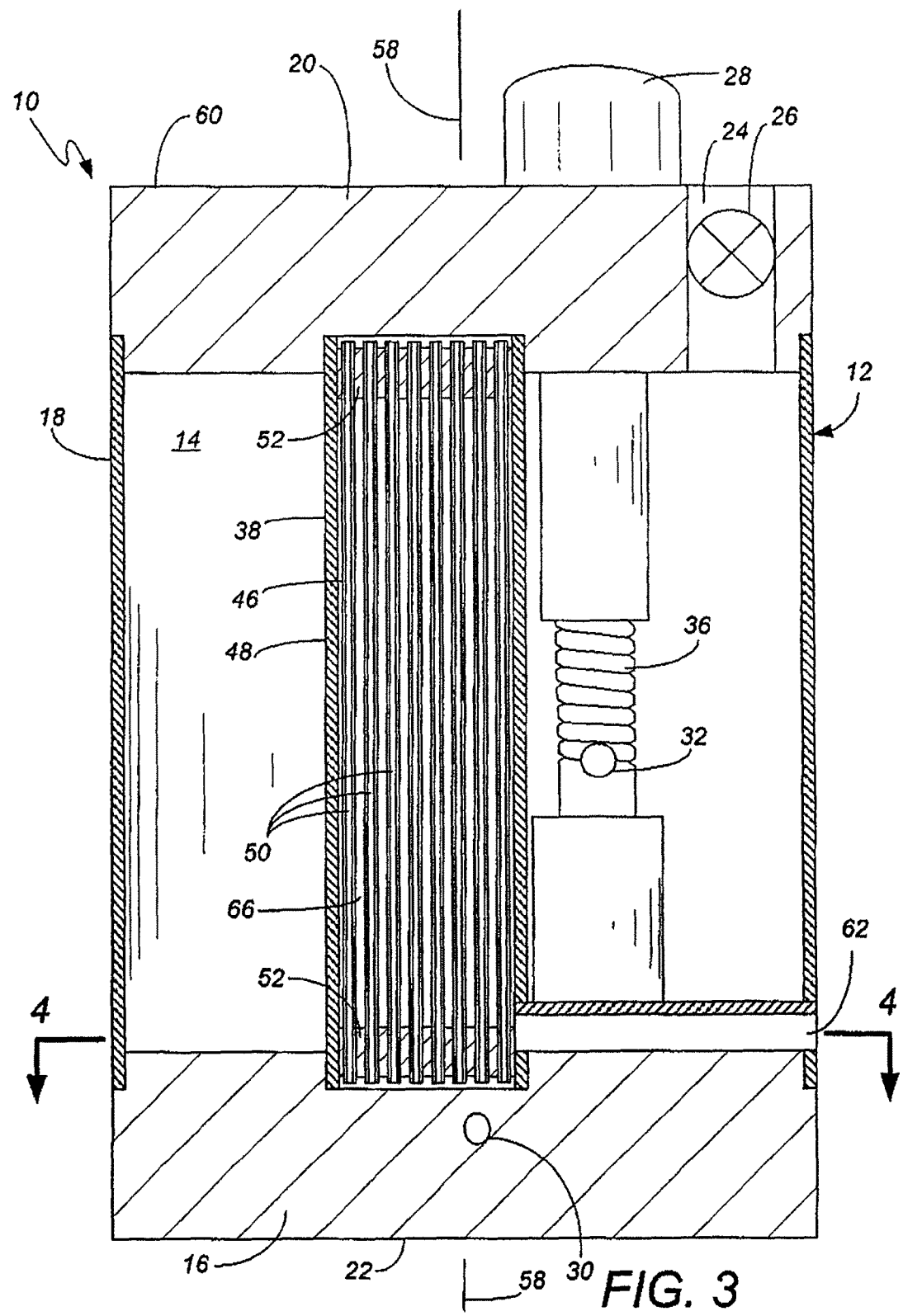
FIG. 3 is a cross-sectional side view of the embodiment of FIG. 1 taken along lines 3-3.
Figure 4:
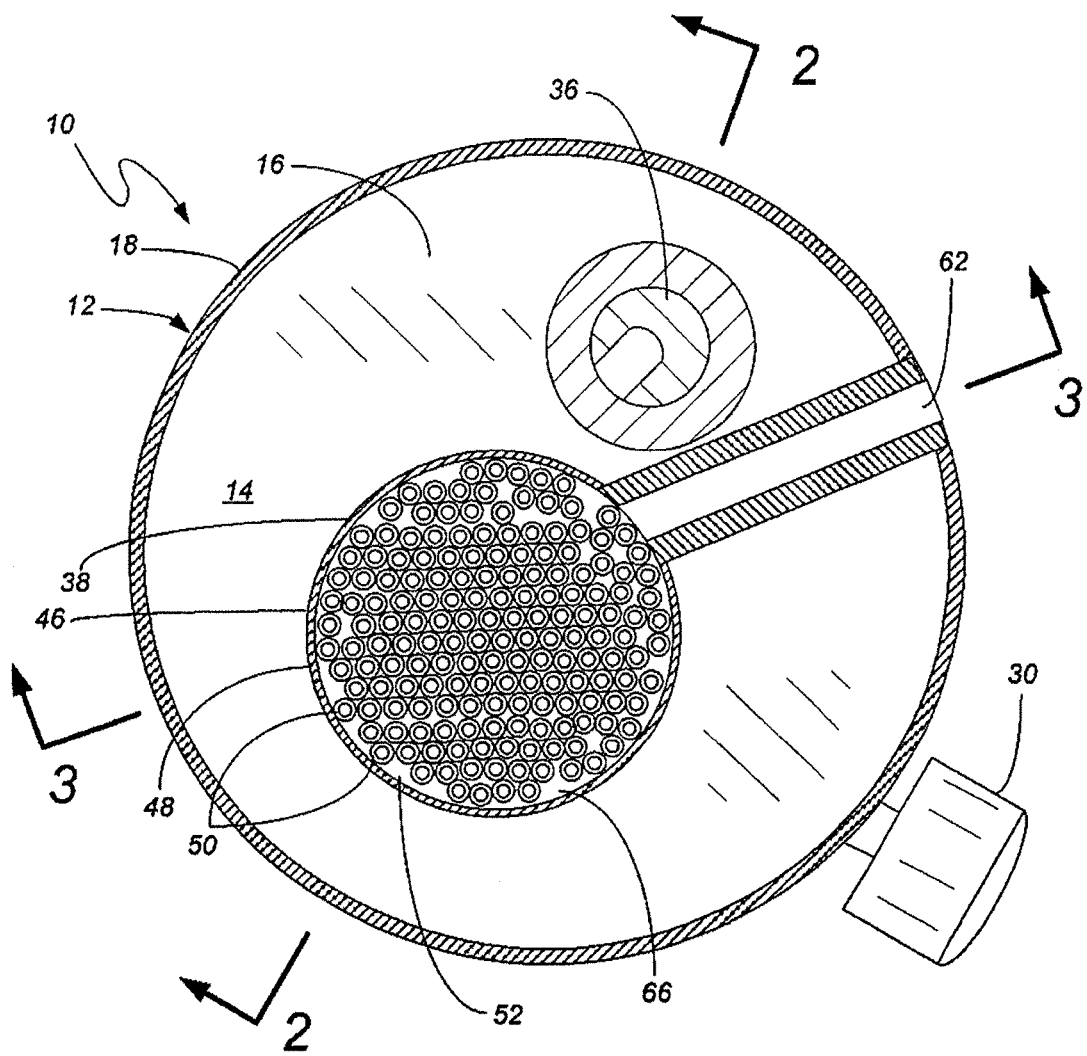
FIG. 4 is a cross-sectional plan view taken along line 4-4 in FIGS. 2 and 3.

As best shown in FIGS. 2-4, the preferred filter 46 includes a filter housing 48 and a filter element, or membrane. The filter element of the present invention comprises a material capable of acting as a separation medium, a filtration medium, or a growth matrix or surface. Separation and/or filtration media include affinity columns, packed bed matrices and beads. Nanofiber networks can be used as filtration media or growth matrix or growth surface. Nanofiber networks and methods of making nanofiber networks are known and commercially available from Surmodics (Minneapolis, Minn.). See, for example, WO 2006/094076, U.S. 2005/0095695 and U.S. 2007/0082393, incorporated herein by reference. In embodiments, the filter element comprises a reaction chamber or holding chamber to collect and retain separated fraction and/or filtered fluids or cells.

In embodiments, the filter element or membrane comprises an affinity membrane, support or column. Affinity columns used in chromatographic separation or purification of proteins and other biological macromolecules make use of specific binding interactions between molecules. In an aspect, a particular ligand is chemically immobilized or "coupled" to a solid support. Ligands that bind to general classes of proteins (such as, for example, receptors or antibodies) or commonly used fusion protein tags (such as, 6×His) are commercially available in pre-immobilized forms ready to use for affinity purification. Alternatively, more specialized ligands such as specific antibodies, antigens or receptors of interest can be immobilized using one of several commercially available activated affinity supports. For example, a peptide antigen can be immobilized to a support and used to purify antibodies that recognize the peptide. Similarly, a receptor that binds a growth factor, differentiation factor, chemotactic factor, or adhesion molecule can be immobilized to a support and used to purify said factors or molecules in the concentrated fraction of body fluids. Antibodies and receptors that bind growth factors, differentiation factors, chemotactic factors, or and/or adhesion molecules, methods of making such antibodies and receptors, and methods of immobilizing the antibodies and receptors on a support are known.

One or more ligands can be attached to a filter element of the invention. The ligands can be selected to bind one or more particular growth factors, differentiation factors, chemotactic factors, and/or adhesion molecules. The ability to attach one or more selected ligands to a filter element of the invention provides for the creation of a custom concentrated body fluid, wherein the particular bioactive molecules comprising the concentrated body fluid are defined, for example, by the particular ligands, concentration of ligands, and/or ratio of one ligand to another selected by the user.

Most commonly, ligands are immobilized or "coupled" directly to a solid support material by formation of covalent chemical bonds between particular functional groups on the ligand and reactive groups on the support. Examples of functional groups and reactive groups include, without limitation, primary amines, sulfhydryls, carboxylic acids, aldehydes, and the like. However, other coupling approaches are also possible. For example, a GST-tagged fusion protein can be first bound to an immobilized glutathione support by affinity interaction with the GST tag and then chemically cross-linked to the support. The immobilized GST-tagged fusion protein can then be used to affinity purify its binding partner(s).

In embodiments, the filter element or membrane comprises affinity or chromatography beads or particles. The beads or particles can be, for example, glass, alginate, polymeric, or magnetic beads or particles. The beads or particles function in the same way as affinity matrices or columns, but are significantly reduced in size, and are therefore particularly useful for microscale biological manipulations. In embodiments, an affinity column or affinity bead or particle is used as the filtration element of the concentrator device such that when a separated fluid or fluid fraction fluid is passed over the beads or particles, those molecules or fluid components that have specific binding affinity to the ligand are retained on the beads, and can be retrieved or isolated by subsequent elution.

In embodiments, the filter element or membrane comprises a packed bed matrix or column. A packed bed is a bed of granular material which retains the solid particles as it passes, allowing fluids and liquids to be filtered free of solid contaminants or components. In an aspect, the granular material for the packed bed can be sand, although celite or diatomaceous earth packed in a microscale container or loaded on top of a sintered-glass funnel can also serve as the packed bed. Incompressible diatomaceous earth (i.e. primarily silica), wood cellulose or other inert porous solids can also be used as the granular material of the packed bed filter. In embodiments, a packed bed matrix or column is used as the filtration element of the concentrator device such that when the separated fluid or fluid fraction is passed over the column, solid components or fluid components with a size greater than the pore size of the packed bed material are retained on the packed bed, while other fluid components pass through.

In embodiments, the filter element or membrane comprises a network of one or more nanofibers, a nanofibrillar structure, glass, silicon, or plastic comprising an etched or micropatterned surface, glass, silicon, or plastic surface comprising macropores or nanopores, or a polymer scaffold. Nanofiber networks of this type are described in WO 2006/094076, U.S. 2005/0059695, and U.S. 2007/0082393, incorporated herein by reference. The nanofiber network can be deposited on a surface of a substrate, and the combination of the nanofiber on the substrate can be a growth matrix or substrate, or as a filtration membrane. In an embodiment, the nanofiber network comprises a fiber diameter of about 30 nm to about 1200 nm, average interfiber spacing of about 100 nm to about 600 nm, and solidity of about 70 percent or less. The nanofibers can be fabricated from a variety of polymers or polymer systems. Preferably the polymer or polymer system is non-cytotoxic. In an embodiment, the nanofibers are fabricated from a polyamide or polyester. The polyamide can be nylon 6, nylon 66, nylon 610 or other biocompatible polyamides. The polyester can be poly($\varepsilon$-caprolactone), poly(lactate) or poly(glycolate). In an embodiment, the polyamide or polyester is suitable for in vivo human application.

The filter element or membrane can also be a nanofibrillar structure comprising one or more nanofibers. The network of one or more nanofibers, as described above, defines the nanofibrillar structure. In an embodiment, the nanofiber network is deposited on a surface of a substrate to provide a growth matrix or surface. In some embodiments, the substrate can be glass, polymeric, metallic, ceramic, cellulosic, or proteinaceous. Examples of a substrate include but are not limited to a rod, screw, wire, mesh, or cage. The substrate can be a surface of a culture container, coverslip, or film. The film can be water soluble or water insoluble, biodegradable or biodissolvable. Preferably the film is non-cytotoxic. In an embodiment, the film comprises polyvinyl alcohol, polychlorotrifluoroethylene, polystyrene, polymethylpentene, or polycylo-olefin. The nanofibrillar structure can be utilized singly or layered to form a multi-layered assembly of nanofibrillar structures for cell or tissue culture. In an embodiment, the nanofibrillar structure comprises a spacer. The spacer can function as a support structure. The spacer provides sufficient openings to permit cells to penetrate and attach to the nanofiber network. The spacer can be water soluble or water insoluble, porous or non-porous, biodegradable or biodissolvable. Preferably the spacer is biocompatible. In embodiments, the nanofibrillar structure is used as a filter element or membrane of the concentrator device, such that when the separated fluid or fluid fraction is passed over the filter element, solid components or fluid components with a size greater than the pore size of the nanofibrillar material are retained on the material, while other fluid components pass through. In other embodiments, the nanofibrillar structure can be a growth matrix, such that when the centrifuged autologous fluid is passed over the filter element, growth factors in the fluid are retained on the element and can be used to support subsequent cell or tissue growth.

In some embodiments, the separation chamber is configured to accept a filter element or membrane of the invention. In such configuration, the filter element or membrane can act as a prefilter to remove unwanted particles or macromolecules from the body fluid prior to separation or during the separation process. In an embodiment, affinity beads or particles that bind a specific molecule, less of molecules, or particular combination of molecules can be used to remove unwanted particles or macromolecules from a fluid. The beads or particles can be added to a biological fluid or body fluid in the separation chamber, or the beads or particles can be added to the separation chamber prior to adding the biological fluid or body fluid to the separation chamber. The beads can be removed before or after separation. In an embodiment, a reagent can be added to the separation chamber or biological or body fluid to precipitate out particles or macromolecules. In an embodiment, the reagent is an antibody or soluble receptor.

In some embodiments, the filter element or membrane of the invention is not tolerant to centrifugation. In such instances, the filter element or membrane is removed from the filter housing 48 and reinstalled into the filter housing 48 after centrifugation.

In an embodiment, the filter membrane has a large number of longitudinally oriented stranded filter lumens 50. The filter strands 50 are sealed with seals 52 to the filter housing 48 at each end. The preferred filter strands 50 are about 3½ inches long, with hundreds of filter strands 50 placed within a ¾ inch diameter filter housing 48, to provide a filter area of about 800 cm$^2$ or more. The filter strands 50 preferably have a pass size of about 10 to 30 kDalton through the lumen wall. With these filter strands 50, the filtrate or retentate moves longitudinally through the lumens 50 and through the filter housing 48, while water and low molecular weight components (genetically called "permeate") pass through the filter membrane 50 transverse to the filter flow direction. Filter strands such as this may be available, for example, from Spectrum Labs of Rancho Dominguez, Calif., or Minntech of Plymouth, Minn.

Figure 5:
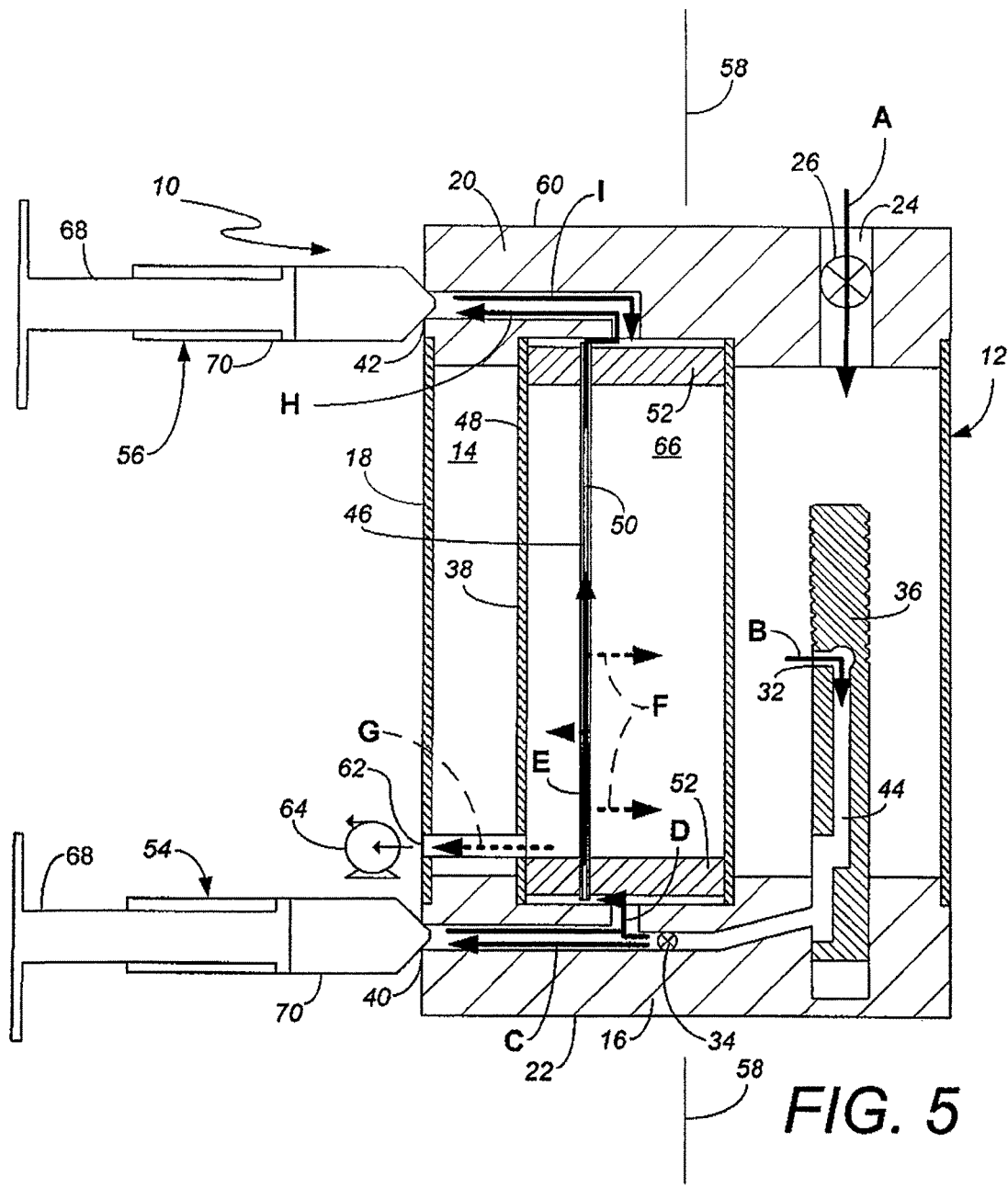
FIG. 5 is a side view of FIGS. 2 and 3, simplified and modified so as to show all functions on a single view, with arrows A-I indicating the stepwise handling of the body fluid through the inventive device.

In an embodiment, if desired, the base port 40 and the top port 42 may include female threads (not shown) to receive transfer syringes 54, 56 shown in FIG. 5. The transfer syringes 54, 56 are used to apply hand controlled pressure to the separator fluid or fluid fraction to push/pull it through the filter 46. If desired, the base port 40 and the top port 42 may be recessed to allow the transfer syringes 54, 56 to extend inward to the location of the ends of the filter 46, thereby minimizing the piping distance (and piping volume) from the transfer syringes 54, 56 to the ends of the filter 46.

In alternate embodiments, the transfer syringes 54, 56 can be operably connected to a pump system used for filtration, such as a vacuum pump system, for example. The pump system applies pressure sufficient to allow fluids to pass through the filter element or membrane, without the application of hand-controlled pressure. The transfer syringes 54, 56 can then be used for transfer of separated or filtered body fluid fractions. In embodiments, the pump system is equipped with a reservoir for the collection and retention of body fluid fractions that have been separated and/or filtered. In other embodiments, a concentration detector is installed in line between the filter element and the pump reservoir. The concentration of a filtered fluid fraction can then be readily measured, to determine if additional concentration is required, or whether the fraction needs to be diluted prior to use. In such an embodiment, the concentration detector can be a light-scattering flow cell, absorbance cell or spectrophotometric device.

In an embodiment, the base port 40 and the top port 42 are disposed on the side of the concentrator 10, oriented transverse to the longitudinal axis 58. This placement allows the base port 40 to be accessible while the concentrator 10 is standing upright on the bottom wall 22 of the base plate 16, and allows the top port 42 to help balance the base port 40 during transfer of the fluid component through the filter 46. Alternatively, the base port 40 and the top port 42 could be slanted relative to the longitudinal axis 58, or even extend through the bottom wall 22 of the base plate 16 and top wall 60 of the top plate 20 parallel to the longitudinal axis 58. Placement of the ports 40, 42 parallel to the longitudinal axis 58 would align the syringe plunger strokes with the direction of fluid movement through the filter 46, thereby reducing the pressure loss due to piping turns and thereby reducing the risk of damaging the fluid during use of the concentrator 10.

As shown in FIGS. 3-5, a vacuum port 62 connects through the main housing 12 and through the filter housing 48. With the vacuum port 62, vacuum pressure 64 (shown schematically in FIG. 4) can be applied to the exterior of the filter strands 50 while the blood component passes through the filter lumens 50. Vacuum sources 64 are commonly available in environments where the concentrator 10 is utilized. If no vacuum source 64 is available, the vacuum port 62 still serves as a gravitational drain to remove water and low molecular weight components that have passed through the filter membrane 50. To help vacuum port 62 act as a gravitational drain, it is placed at the bottom of the filter chamber 66.

In an embodiment, the filter housing 48 is sealed to eliminate fluid communication between the separation chamber 14 and the filter chamber 66. Alternatively, the filter housing 48 may be open to the separation chamber 14, such that the water and low molecular weight components which pass through the filter membrane 50 proceed into the separation chamber 14. If the filter housing 48 permits fluid communication between the filter chamber 66 and the separation chamber 14, then the vacuum port 62 will serve to remove or drain the desired fluid fraction or component as well as water and other low molecular weight components from the concentrator 10.

The use of the invention is described with respect to the lettered steps shown in FIG. 5. In an embodiment, a sample of body fluid (approximately 60 to 80 mL) is placed through the inlet closure 26 and into the separation chamber 14 as shown by arrow A. Preferably, this occurs within minutes after the fluid is withdrawn from the patient. Different amounts or different types of fluid can be alternatively used if the concentrator 10 is used for a different concentration purpose.

In an embodiment, once the entire fluid sample is within the separation chamber 14, the inlet closure 26 is closed, and the concentrator 10 is centrifuged. The centrifugation process is performed in accordance with known centrifuge strategies and velocities, as further described below.

After centrifugation or gravitational weight separation is complete, the fluid has separated into different layers, which may be visually discernable by viewing through the central housing 18. Transfer syringes 54, 56 are attached to the base port 40 and the top port 42. The valve adjustment handle 28 is rotated until the height of the valve inlet 32 lines up with the bottom of the fluid layer(s) desired to be further processed. The valve 34 is opened using the valve control handle 30, while the desired fluid layer(s) drain into the base plate 16 and the bottom syringe 54 as shown by arrows B and C. If necessary for pressure relief to enable all of the desired fluid layers to be removed from the separation chamber 14, the inlet closure 26 may be opened slightly during draining of the desired fluid layers through the valve 34. Preferably, however, the inlet closure 26 will incorporate a valve (not shown) allowing for pressure release. Once the desired fluid layer(s) have been extracted, the valve control handle 30 is used to close off the valve 34. The unwanted layers are retained in the separation chamber 14.

Vacuum pressure is now applied to the vacuum port 62. Because the remainder of the concentration procedure does not rely on gravitational weight separation, the concentrator 10 device may be placed on its side if desired. The vacuum port 62 is preferably located on a side of the central housing 18 opposite the transfer ports 40, 42, thereby providing counterweight and stabilization during 30 transfer of the desired fluid layer(s) through the filter 46. The plunger 68 on the bottom syringe 54 is pushed (while the plunger 68 on the top syringe 56 is optionally being pulled), pushing the desired fluid upward and into the top syringe 56 as shown by arrows D and E. Water, low molecular weight elements and any other unwanted components of the desired fluid are removed through the filter strands 50, as shown by arrows F, and then drained through the vacuum port 62 as shown by arrow G. The desired fluid passes through the filter strands 50 and into the top syringe 56 as shown by arrow H, becoming "first pass concentrated".

In an embodiment, the volume of the piping 44 from the valve inlet 32 to the filter 46, including the bottom syringe 54, is minimized so as to get as great a yield of concentrated desired fluid from a single starting sample as possible. If desired, the top port 42 and the base port 40 may include recesses to receive a greater length of the transfer syringes 54, 56, and thereby minimize the distance from the end of the transfer syringes 54, 56 to the inlets to the filter housing 48.

The first pass concentrated fluid can be further concentrated by reverse filtering. The plunger 68 on the top syringe 56 is pushed (while the plunger 68 on the bottom syringe 54 is optionally pulled), thereby pushing the first-pass concentrated fluid through the filter 46 as shown by arrow I and into the bottom syringe 54. Additional water and low molecular weight components are withdrawn from the first-pass concentrated fluid (arrows F and G). The reverse filtering makes additional use of the filter element or membrane 50 and further concentrates the first pass concentrated fluid into "second pass concentrated" fluid. If desired, additional passes may be performed in a like manner.

The concentrated fluid may be used immediately or after further preparation such as mixing the concentrated fluid with other components, growth factors, differentiate factors, chemotactic factors, and/or adhesion factors suitable for use in various applications. For example, where blood is autologous fluid, the concentrated fluid is mixed with thrombin and then brushed it onto an implant's surface.

In an embodiment, the stranded filters 50 used are single use filter elements, which cannot be effectively cleaned and sterilized. Accordingly, the filter element 46 is disposed of after its single use. In an embodiment, the entire separation/filtering vessel 10 is sufficiently inexpensive that the entire concentrator 10 unit can be discarded after a single use. This simplifies and/or avoids cleaning of the separation unit and/or filter housing 48. This also simplifies disposal of the undesired fluid components.

Filtering within the separation vessel provides further advantages which can be achieved in alternative embodiments. For instance, if the inlet 32 for the drain valve 34 is automatically (rather than visually) positioned at the proper height for the desired fluid layer(s), then the drain valve 34 could be automatically opened using centrifugally activated valves as known in the art. Using similar arrangements, the desired fluid layer(s) can be passed through the filter 46 during centrifugation, using centrifugal forces to push/pull the desired fluid layer(s) through the filter 46.

In an embodiment, the filter 46 is oriented longitudinally with respect to the centrifugation direction (i.e., with respect to longitudinal axis 58). This helps minimize the possibility that the filter strands 50 might pull from their end seals 52 and/or break during centrifugation. Alternative embodiments could include orienting the filter strands 50 transversely and at the general height of the desired fluid layer(s), thereby further reducing the piping volume needed to transfer the desired fluid layer(s) to the filter 46.

In an embodiment, external syringes 54, 56 are utilized to provide the transfer pressure force for pushing/pulling the desired fluid layer(s) through the filter 46. This provides a low cost method of applying such forces. In an embodiment, syringes 54, 56 permit the surgeon to control the amount of pressure versus time on the filtration chamber 66 to force a selected amount of water and low molecular weight components of the centrifuged fraction through the filter membrane 50. As an alternative to the use of external syringes, the syringes 54, 56 (including particularly the plunger 68 and slide tube elements 70) could be fabricated and/or attached as part of the device. For instance, the bottom wall 22 of the base plate 16 and the top wall 60 of the top plate 20 could be slidable or depressible similar to the plunger on a syringe, to thereby apply the transfer pressure to push/pull the desired fluid layer(s) through the filter 46. The use of syringes 54, 56 also allows for the force pushing the desired fluid layer(s) through the filter 46 to be hand controlled by the surgeon or other operator.

Figure 6:
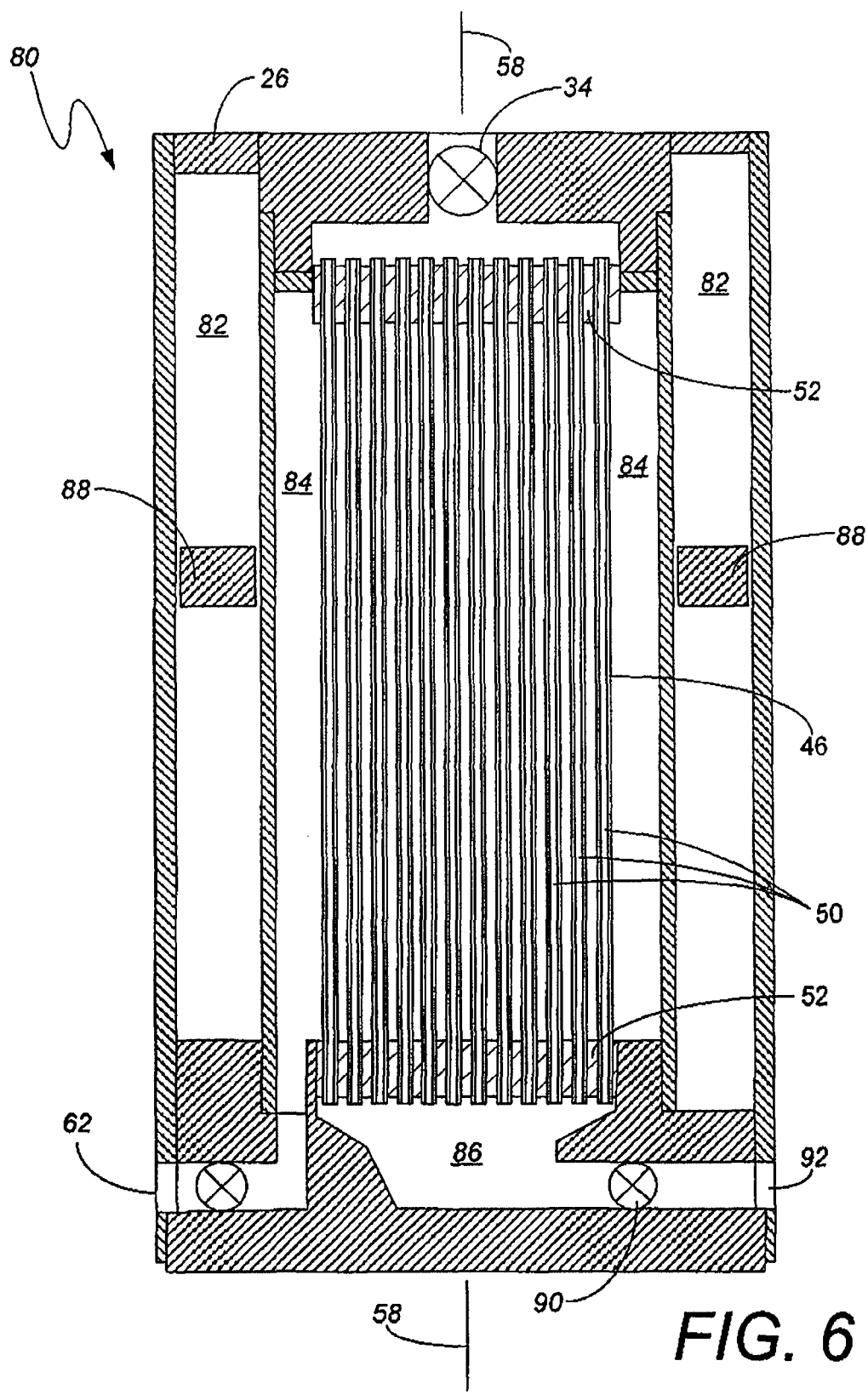
FIG. 6 is a cross-sectional side view of a second embodiment of the invention.

An additional embodiment of the invention is shown in the concentrator 80 of FIG. 6. Similar to the first embodiment 10, the same vessel used in separation is also used to provide filtration. In an embodiment, fluid is centrifuged in the concentrator vessel 80 or subjected to gravitational weight separation in the concentration vessel 80, and then positive or negative pressure is applied in the same concentrator vessel 80 after separation to force water, low molecular weight components, and other undesired components from the separated fraction resulting in a first pass concentrated component.

The concentrator vessel 80 includes three chambers 82, 84, 86. A separation chamber 82 holds the fluid during separation. A water chamber 84 receives water, low molecular weight components and other undesired components removed from the desired fluid layer(s) through the filter 46. A concentrated fluid chamber 86 receives the concentrated fluid which has been filtered.

The separation chamber 82 preferably holds a float 88 of a particular specific gravity, such as generally equal to the specific gravity of buffy coat. The float 88 can be used to aid in positioning of a syringe (not shown) during transfer of the desired fluid layer(s) from the centrifuge chamber 82 to the filter 46. Alternatively, openings in the float 88 can be provided to permit fluid fraction flow therethrough during centrifugation.

The "shut off" valve 90 for the concentrated fluid chamber 86 may be a variable position valve that would allow the operator to "dial in" the maximum pressure that could be generated in the concentrated fluid chamber 86, and/or the maximum pressure differential between the water chamber 84 and the concentrated fluid chamber 86, thereby controlling the concentration of the final output. For example, the shut off valve 90 may include a dial with three or more positions connected to something like a butterfly valve or regulator valve, such that the operator selects the desired concentration on the dial then pressurizes the desired fluid layer(s) through the filter 46 to the selected pressure/concentration level. Depending on the dial position selected, a predetermined pressure is generated across the filter 46 that allows for the corresponding amount of water to be removed, thus delivering the desired concentration in one stroke and without the need to fully close off the outport 92.

Figure 7:
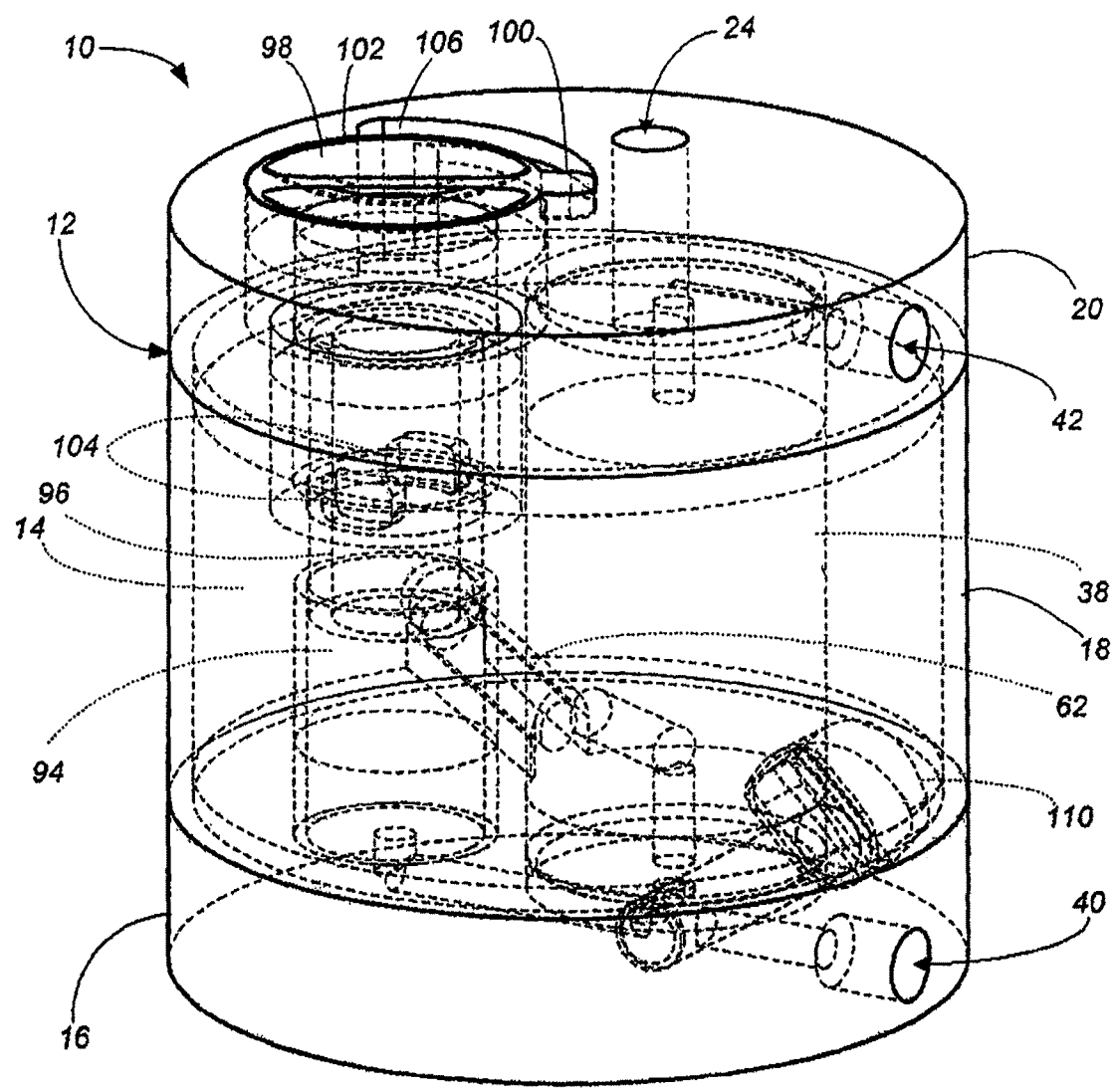
FIG. 7 is a perspective view of a third embodiment of the invention, showing hidden detail in dashed lines.
Figure 8:
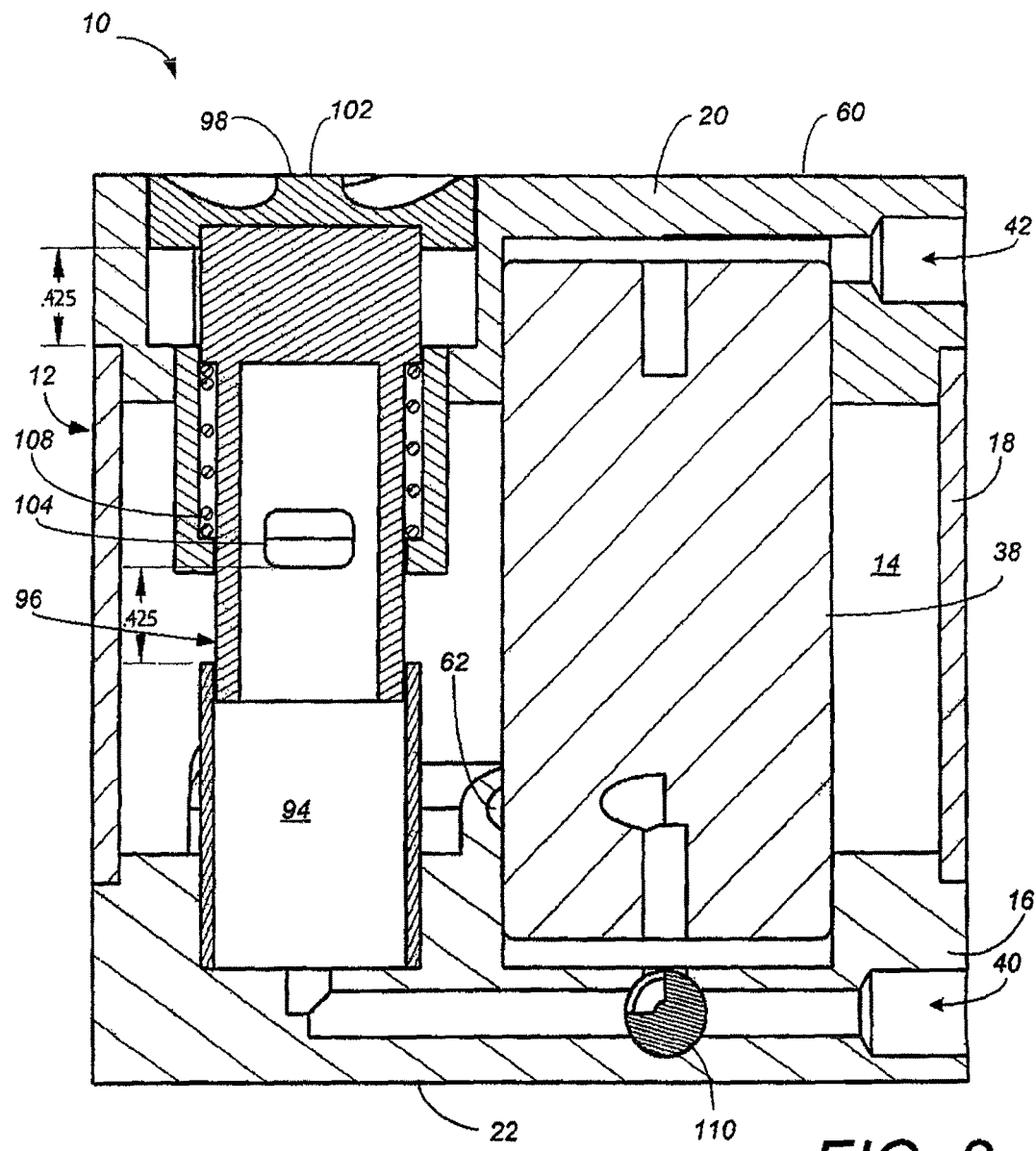
FIG. 8 is a cross-sectional view of the embodiment of FIG. 7.

In a third embodiment shown in FIGS. 7 and 8, a desired fluid layer(s) isolation chamber 94 is defined between the separation chamber 14 and the filter unit 38. Also, a window valve 96 is added between the separation chamber 14 and the isolation chamber 94. The window valve 96 is ordinarily closed, preventing fluid communication between the separation chamber 14 and the isolation chamber 94. Thus, while the starting fluid sample is in the separation chamber 14 and during separation, there is no possibility of the starting fluid passing through the window valve 96 and into the isolation chamber 94 (or into other piping between the separation chamber 14 and the filter unit 38 such as piping 44 in the first embodiment).

In an embodiment, the window valve 96 has a locking mechanism 98, which also acts as a valve handle. A lock 100 prevents the lock handle knob 102 from being pushed down, thereby preventing the windows 104 from being pushed down into communication with the separation 14 during separation, such as. Once separation is complete, the lock handle knob 102 is rotated 90° to a position where the lock 100 lines up with a keyway 106, enabling the knob 102 to be pushed downward against a spring 108. The windows 104 are attached to and controlled by the knob 102, and pushing the lock handle knob 102 downward moves the windows 104 downward into communication with the separation chamber 14. When the windows 104 are open to the separation chamber 14, the desired fluid layer(s) of the separated fluid flow by gravity from the separation chamber 14 into the isolation chamber 94. Once the desired fluid layer(s) have drained into the isolation chamber 94, the knob 102 is released, with the spring 108 moving the windows 104 upward and closing communication between the isolation chamber 94 and the separation chamber 14.

The isolation chamber 94 holds the desired fluid layer(s) until subsequent processing, such as filtration. The isolation chamber 94 defines the volume of the desired fluid layer(s) which will be removed from the starting fluid unit and filtered. Placement of the desired fluid layer(s) within the isolation chamber 94 allows the concentrator 10 to be handled without fear of remixing the desired fluid layer(s) into the remainder of the starting fluid. For example, after the desired fluid layers(s) are moved into the isolation chamber, the concentrator 10 can be placed on its side prior to fluid filtration. The isolation chamber 94 also permits a delay time between separation and filtering. The desired fluid layer(s) can optionally be further treated while in the isolation chamber 94. For example, additives may be mixed with the fluid within the isolation chamber 94, particularly if the additives enhance the filtration process, such as by having the additives in the isolation chamber 94 prior to opening the window valve 96.

A twist valve 110 is opened to open communication between the isolation chamber 94 and the base port 40 and the filter unit 38. The desired fluid layer(s) are withdrawn from the isolation chamber 94 through the twist valve 110 with a syringe 54, at which point the twist valve 110 is closed. The plunger stroke on the syringe 54 is then reversed to push the desired fluid layer(s) through the filter unit 38. If desired, the syringes 54, 56 for pressuring the fluid layer(s) through the filter unit 38 can have a much lower volume than the isolation chamber 94 (say, for instance, ⅓ the volume). Then fluid can be removed from the isolation chamber 94 in portions (⅓ at a time) which are filtered separately, one portion at a time. Portioning of the desired fluid layer(s) through the filter unit 38 is particularly advantageous in situations wherein preparation steps are taken for the filter 46 between portions. For instance, if the filter 46 is becoming clogged while only filtering ⅓ of the fluid volume in the isolation chamber 94, a purge fluid could be pressured through the filter 46 to unclog the filter 46 prior to filtering the second portion through the filter 46. After the first portion has been filtered and the filter 46 purged, the twist valve 110 is reopened to remove a second portion. The twist valve 110 is then reclosed to permit filtering of the second portion, followed by any purging of the filter 46. Because the twist valve 110 controls communication between the isolation chamber 94 and the base port 40, fluid may thus be removed from the isolation chamber 94 in whatever size portions are desired.

In another embodiment (not shown), a syringe having a plunger is provided to pull (negative pressure) the component out of the centrifuged starting fluid (i.e. the original fluid sample). The syringe also houses a filter 46, and the plunger stroke is reversed to push (positive pressure) the component through the filter 46 and separate the component into water and a concentrated retentate.

In all these embodiments, the surgeon or other operator controls the pressure and/or duration of the filtration step, and thus the surgeon or other operator controls how concentrated the concentrated retentate is relative to the separated component, as well as how hard the fluid is worked during the filtration step.

B. Protein Separation and Concentrated Autologous Fluids

A concentrator device of the invention can be used to separate organelles, cells or proteins, in addition to concentrating body fluids. Separation can be performed by centrifugation or gravitational weight separation. In some embodiments, the body fluids may be autologous body fluids. Centrifugation is a process used to separate or concentrate materials suspended in a liquid medium. The theoretical basis of this technique is the effect of gravity on particles (including macromolecules) in suspension. Two particles of different masses will settle in a tube at different rates in response to gravity. Centrifugal force (g) is used to increase this settling rate, and the means to increase the rate is a centrifuge. The centrifugal force generated is proportional to the rotation rate of the rotor (in RPM) and the distance between the rotor center and the centrifuge tube. Therefore, a given centrifuge may use multiple rotor sizes to give flexibility in choosing centrifugation conditions.

Rotors for centrifuge devices are either fixed angle, swinging bucket, continuous flow, or zonal, depending upon whether the sample is held at a given angle to the rotation plane, is allowed to swing out on a pivot and into the plane of rotation, designed with inlet and outlet ports for separation of large volumes, or a combination of these. In embodiments, the methods of the present invention use continuous flow centrifugation for separation and concentration of large fluid volumes. Continuous flow centrifugation can also be used for the large scale separation of particles on density gradients. These rotors can contain up to 2 L of fluid and can work with tissue samples measured in ounces. The rotors are brought up to about 3000 RPM while empty, and the density media and tissues are added through specialized ports. This type of rotor has a distinct preparative advantage over the gradient capacity of more typical rotors. In embodiments, the rotors are used in ultracentrifugation processes, and contain small volumes of fluid, up to 250 mL. The rotors can be used for laboratory manipulations where only small fluid volumes or tissue amounts are available. For ultracentrifugation, the rotors are brought up to 15,000-18,000 RPM with a maximum of 20,000 RPM. Rotors for standard centrifugation can range from 4 by 2 or 2.5 L to 40 by 250 μL. For ultracentrifugation applications, rotors can range from 6 by 250 mL to 72 by 230 μL, with wide intermediate ranges such as, for example, 8 by 6.8 mL, 6 by 94 mL, 6 by 4 mL, 8 by 5.1 mL, and 8 by 39 mL. The main housing of a fluid concentrator of the invention can be dimensioned to mate and be received by a standard centrifugation rotor or ultracentrifugation rotor. As with standard centrifugation, the rotors can be brought up to speed while empty, with the media, samples and tissues introduced through special ports.

The concentrator of the invention can be used to separate proteins or cells by density gradient centrifugation. The use of density gradients is routine in centrifugal fractionation of particle mixtures, cells mixtures, and purification of subcellular organelles and macromolecules, including proteins. A particle can be a macromolecule or cell. The mixture of particles to be separated is placed onto the surface of a vertical column of liquid, the density of which progressively increases from top to bottom, and then centrifuged. Although the particles in suspension are individually denser than the liquid at the top of the gradient, the average density for the sample (i.e. particles plus suspending liquid) is lower. The two main types of density gradient centrifugation are rate-zonal separation and isopynic separation. In rate-zonal separation particles are separated based on their size and mass. The particles migrate through the gradient until they reach the point at which their size and mass match that of the gradient. This centrifugation method is useful in separating out particles with the same or very similar densities, but different masses. Many proteins, such as antibodies, for example, may be separated in this way. Protein separation by centrifugation can be predicted by simulation software, such as EPS Rate Zonal Run (Beckman Coulter, Fullerton, Calif.). In isopycnic separation the particles migrate through the solvent gradient until they reach the point where their density is equal to that of the gradient, i.e. the isopycnic point. Once the particles have reached their isopycnic point they will no longer move in the gradient, regardless of how much longer the centrifuge is run for. Isopycnic gradients include cesium chloride gradients, for example.

Density gradients can be used to affect protein or cell separation using a concentrator device of the invention. There are two types of density gradients: stepwise gradients and continuous gradients. Step gradients are prepared by successively layering solutions of different density in the centrifuge chamber and then layering the sample to be fractionated on top of the last "step". Step gradients are useful in density gradient centrifugation because the abrupt density steps can be used as surfaces on which particles can sediment during centrifugation. This results in discrete particle layers at each step. The gradient can be built up in the centrifuge rotors or tubes, carefully layering one step on another, beginning with the densest step, by use of a pipette, or other mechanical or syringe means. Alternatively the gradient can be formed beginning with the least dense step by depositing each layer at the bottom of the centrifuge chamber through a narrow cannula or by other mechanical or syringe means. Continuous density gradients are gradients in which the density changes smoothly and continuously from one limit or extreme to another. Such gradients can be produced from step gradients by allowing sufficient time for diffusion to smooth out the steps, but continuous gradients are normally prepared directly by using special devices known as gradient makers or gradient engines.

Body fluids can be concentrated using a concentrator device of the invention by density gradient methods. In embodiments, the body fluids are autologous body fluids. At the conclusion of centrifugation, the density gradient and the separated particles, cells or proteins and desired fluid layer(s) can be removed from the rotor and collected as a series of fractions.

In embodiments, one or more fluid fractions collected from the concentrator device correspond to concentrated body fluids. Various different concentrated body fluids can be prepared by centrifugation or gravitational weight separation including, without limitation, blood fractions (platelet rich plasma (PRP), platelet poor plasma (PPP)), stem cells (cord blood-derived and bone marrow-derived) for example, concentrated seminal fluid, concentrated spinal fluid and the like.

In an embodiment, the fluid fractions are concentrated to concentrations of about 1:10, about 1:20, about 1:30, about 1:40, about 1:50, about 1:100, about 1:200, about 1:500, or about 1:1000. In an embodiment, the one or more components in a concentrated fluid fraction is concentrated about 1:10, about 1:20, about 1:30, about 1:40, about 1:50, about 1:100, about 1:200, about 1:500, or about 1:1000 compared to the same one or more components in the unconcentrated fluid. In an embodiment, the fluid fractions are concentrated to concentrations from about 1:20 to about 1:50, from about 1:20 to about 1:100, from about 1:50 to about 1:100, from about 1:50 to about 1:200, from about 1:100 to about 1:200, from about 1:200 to about 1:500, from about 1:200 to about 1:1000, or from about 1:500 to about 1:1000. In an embodiment, one or more components in a concentrated fluid fraction is concentrated from about 1:20 to about 1:50, from about 1:20 to about 1:100, from about 1:50 to about 1:100, from about 1:50 to about 1:200, from about 1:100 to about 1:200, from about 1:200 to about 1:500, from about 1:200 to about 1:1000, or from about 1:500 to about 1:1000 compared to the same one or more components in the unconcentrated fluid. In some embodiments, the concentrator of the invention preserves or maintains the physiological ratios of the components in the body fluid fraction. The exact ratio of each component is not significant, as long as the relative physiological ratios are maintained during concentration.

In an embodiment, a concentrated and filtered fraction of autologous fluid obtained by a concentration device of the invention is administered to a subject within about 5 minutes, about 10 minutes, about 20 minutes, about 30 minutes, about 40 minutes, about 50 minutes, about 60 minutes, about 1.5 hours, about 2 hours, about 2.5 hours, about 3 hours, about 3.5 hours, or about 4 hours from the time of isolation of the antilogous fluid from the subject.

Uses and Methods of the Invention

Concentrated body fluids obtained by the methods of the invention can be used in a wide variety of applications, including, without limitation, surgical applications, preparation of allograft materials for implants, tissue regeneration or tissue culture, stem cell growth or separation, seminal fluid fractionation, protein separation, and DNA purification. In embodiments, the concentrated biological fluids of the invention are autologous body fluids.

Surgical Uses

The concentrator of the invention can be used to obtain concentrated fractions of blood or plasma, including platelet rich plasma (PRP) and platelet poor plasma (PPP). In embodiments, the concentrator of the invention is used to obtain concentrated PRP from a sample of patient blood during surgery for use in surgical applications, such as bone healing. In an embodiment, whole blood is withdrawn from the patient, and centrifuged in the concentrator of the invention for 5 to 30 minutes at 25 to 1000 g, and in another embodiment, the whole blood is centrifuged for about 15 minutes at 400 g. The central PRP layer of the centrifuged blood is visually identified by color and withdrawn from the separation chamber. The PRP layer is passed through the filter unit under syringe pressure for one to ten passes, and in an embodiment, the PRP layer is passed through the filter for 6 passes. The filtration can be tangential flow or dead end. In an embodiment, tangential flow filtration using hollow filter fiber membranes with a size cutoff of 0.1 nm to 100,000 nm and a surface area of 1 cm$^2$ to 6000 cm$^2$ is used. This results in the production of concentrated PRP. The concentrated PRP obtained has a thick, gel-like consistency, having an increased concentration of platelets and white blood cells as compared to whole blood. With the higher concentration of platelets, the resultant material includes a higher concentration of growth factors from the blood. The resultant concentrated PRP product can be directly applied to, for example, a fractured or damaged bone during surgery, a wound, a surgical incision, or damaged tissue. In an embodiment, the concentrated PRP obtained by the concentrator can be a bone growth stimulant applied directly to the injured or fractured bone, wound, surgical incision or damaged tissue. The higher concentration of the patient's own growth factors obtained from the patient's blood induce a faster healing rate for the bone, reduce low grade infection around the surgical site or wound, and reduce soft tissue inflammatory response. If desired, various known diluents, such as buffered saline, may be used to adjust the viscosity of the autologous concentrated PRP for various applications.

In other embodiments, a concentrator of the invention is used to obtain concentrated PRP from a sample of patient blood during surgery, for use in surgical applications such as cartilage healing. The resultant concentrated PRP product is surgically applied directly to a site of damaged, wounded or severed cartilage. If desired, the concentrated PRP can be mixed with chondrocytes obtained from the patient or a different source. In an embodiment, chondrocytes are isolated by sequential enzymatic digestion of full-thickness articular cartilage with pronase and collagenase. In an embodiment, the cartilage is autogenic/autologous, allogenic or xenogenic. In an embodiment, the cartilage is derived from mammalian sources, including human, porcine and bovine sources. The concentrated PRP can also be mixed with artificial polymer or collagen-based cartilage replacement products to improve integration of the cartilage defect repair substance and to enhance anchoring of the cartilage defect repair substance.

By applying the concentrated PRP obtained by the concentrator of the invention as a cartilage repair growth stimulant directly to the cartilage site, the higher concentration of growth factors obtained induces a faster healing and ingrowth rate for the cartilage, reduce low grade infection around the surgical site, and reduce soft tissue inflammatory response. In an embodiment, the concentrated PRP is an autologous fluid obtained from the patient's own blood.

In some embodiments, concentrated PRP is obtained as described above, and the concentrated PRP is applied either between two locations of soft tissue such as at a surgical incision, in between stitched tissue, etc., or as a salve or balm over a section of damaged soft tissue, such as over a burn site, laceration or abrasion. Concentrated PRP used as a salve or balm causes delivery of additional growth factors and blood proteins to the tissue healing site, resulting in faster wound closure and healing. While not wishing to be bound by a particular theory, it is believed that the concentrated PRP used in a salve or balm for soft tissue healing induces or promotes an effective increase in one or more of cytoplasmic granules, serotonin, ADP, Thromboxane A$_2$, factors III, V, VII, X, XI and/or XII, platelet thromboplastic factor (PF$_3$), and prothrombin activator.

In some embodiments, the concentrated PRP of the invention is used as platelet glue wound sealants. These sealants are discussed in U.S. Pat. Nos. 5,733,545; 6,010,627; and 6,342,157, incorporated by reference. Concentrated PRP can be obtained by a concentrator of the invention as described above. The resultant concentrated PRP is a sticky gel-like material, which can be used similar to surgical glue to adhere two tissue portions together.

If desired, concentrated PRP of the invention can be mixed with other surgical glue materials to increase the adhesive characteristics, increase the yield volume, and/or adjust the spreadability of the resultant mixture. For instance, a common class of tissue adhesives is fibrin-based and contains a concentrate of fibrinogen and thrombin. The fibrin adhesives are typically two-component adhesives that when mixed together react to simulate the last stages of the clot-forming cascade. The resulting clot adheres to tissue and bridges a gap therebetween until healing can occur. The concentrated PRP of the present invention can be mixed with any of these known biologically presourced, tissue adhesives.

The concentrated PRP in the surgical glue causes delivery of additional growth factors and blood proteins to the tissue healing site, resulting in faster wound closure and healing. While not wishing to be bound by a particular theory, it is believed that the concentrated PRP used in a salve or balm for soft tissue healing induces or promotes an effective increase in one or more of cytoplasmic granules, as described above with regard to concentrated PRP used as a salve or balm.

In some embodiments, other fluids, including platelet poor plasma (PPP) can be used as surgical glue materials. For example, the concentrator of the invention is used to obtain concentrated PPP from a sample of patient blood during surgery. In an embodiment, whole blood is withdrawn from the patient, and centrifuged in the concentrator of the invention for 2 to 30 minutes at 250 to 10000 g. In another embodiment, withdrawn blood from the patient is centrifuged in the concentrator of the invention for about 5 minutes at 6500 g. The PPP layer of the centrifuged blood is visually identified by color and withdrawn from the centrifuge chamber. The PPP is passed through the filter unit under syringe pressure for one to ten passes, and in an embodiment, for 4 passes. If desired, the PPP can be cooled prior to filtration to accelerate precipitation separation, such as down to 1 to 10° C. The filtration results in a concentrated PPP. The concentrated PPP obtained is a viscous liquid, having an increased concentration of fibrinogen, thrombin, clotting factors and associated proteins and structures as compared to whole blood. Various known diluents, such as buffered saline, can be used to adjust the viscosity of the autologous concentrated PPP for various applications.

The resultant concentrated PPP product can be used as an essential ingredient in formulating a high fibrin glue. If a cooling step was applied to the platelet poor plasma, the high fibrin glue can be reheated to about 37° C. for application to the patient.

If desired, the high fibrin glue can be mixed with commercially available sealant preparations, such as TISSEEL from Baxter International of Deerfield, Ill. or with cyanoacrylate tissue adhesives such as DERMABOND of Ethicon of Somerville, N.J. The high fibrin glue helps produce a stable, flexible and elastic fibrin bioactive matrix, which firmly adheres to exposed collagen, similar to those formed more slowly during physiologic blood coagulation. The autologous PPP glue of the present invention can also be mixed with glues based on gelatin cross-linked with an aldehyde, such as gelatin-resorcinol cross-linked with formaldehyde (GRF) or glutaraldehyde (GRFG), or with tissue glues derived from cyanoacrylates, polyurethanes, polymethylmethacrylates, among other synthetic polymers.

The high fibrin glue can be used during surgery, such as during thoracic, cardiovascular, and general surgical operations, and in orthopedic procedures such as fixation of chondral fragments, chondral chips and osteochondral fragments. The high fibrin glue can also be used as an adjunct to hemostasis in surgeries involving cardiopulmonary bypass and treatment of splenic injuries due to blunt or penetrating trauma to the abdomen, when control of bleeding is important. The high fibrin glue can also be used for incisional or laceration repair. These uses of fibrin glue in accordance with the invention provide a flexible water-resistant protective coating to the repaired tissue and may eliminate the need for suture removal. The high fibrin glue can also be used to adhere drug delivery matrices, or other such overlays that can be used in conjunction with autograft, allograft, or xenograft materials, such as ligaments, bone tissue, skin, tendons, cartilage and the like.

In some embodiments, concentrated PPP obtained by the methods of the invention is used for cartilage healing. Concentrated PPP is obtained as described above. The concentrated PPP can be applied as a cartilaginous repair material directly to a cartilage defect. If desired, the concentrated PRP can be mixed with chondrocytes obtained from the patient or a different source. In an embodiment, chondrocytes are isolated by sequential enzymatic digestion of full-thickness articular cartilage with pronase and collagenase. The concentrated PPP can also be mixed with artificial polymer or collagen-based cartilage replacement products to improve integration of the cartilage defect repair substance and to enhance anchoring of the cartilage defect repair substance.

Graft Materials

A concentrator of the invention can be used, for example, to obtain concentrated fluids or concentrated autologous fluids such as autologous concentrated PRP, PPP, growth factors, differentiation factors, chemotactic factors, adhesion molecules, or stem cells for use in surgical applications. In an embodiment, a graft material is an allogenic or xenogenic material, derived from mammalian sources including human, bovine and porcine sources. In an embodiment, autologous concentrated PRP, PPP, growth factors, differentiation factors, chemotactic factors, adhesion molecules, stem cells, or a combination thereof are applied to an organ or tissue from a genetically non-identical donor prior to or during transplanting of the organ or tissue. Such application to the allograft or xenograft results in increased acceptance of the new organ or tissue from the recipient's immune system and decreased rejection, aids in regeneration of tissue around the new organ or tissue, and further helps decrease healing time from the transplant surgery.

A concentrator of the invention can be used to obtain a concentrated fluid containing one or more growth factors, differentiation factors, chemotactic factors, adhesion molecules or a combination thereof from a body fluid for use in the preparation of graft materials for implantation. In an embodiment, the concentrated fluid is PRP, PPP, or PRP+PPP. In an embodiment, the concentrated fluid is autologous. The graft material can be coated to provide controlled release of proteins such as one or more growth factors, differentiation factors, chemotactic factors, adhesion molecules, or combination thereof from a surface of the graft material. The graft material can be coated with a layer of polymeric material. Solubility or insolubility of the polymeric material can be engineered to control the release of the one or more growth factors, differentiation factors, chemotactic factors, adhesions molecule, or combination thereof of bioactive molecules from the polymeric coating. In an embodiment, the rate of release is determined by the rate of degradation and/or dissolution of the polymer or copolymer comprising the coating.

In an embodiment, the polymer layer comprises one or more reactive functional groups that can react with or covalently bind one or more growth factors, differentiation factors, chemotactic factors, adhesion molecules, or a combination thereof present in the concentrated autologous fluid. Examples of suitable polymeric materials include but are not limited to EUREKA DUET in-situ forming matrix, EUREKA DUET biodegradable device matrix, ENCORE drug delivery polymer matrix, SYNBIOSYS biodegradable drug delivery polymer system, CAMEO biodegradable polymeric drug delivery matrix, POLYACTIVE biodegradable polymeric drug delivery matrix, CELLABRATION encapsulation polymer matrix, and PHOTOLINK (Surmodics, Minneapolis, Minn.). The concentrated body fluid or autologous fluid can be used to reconstitute graft material, which is typically in a freeze-dried form. Reconstituting the graft material with an autologous concentrated fluid such as PRP provides increased acceptance of the tissue at the transplant site and speeds healing after graft surgery.

In other embodiments, a coating agent comprises a nonpolymeric core molecule having attached thereto, either directly or indirectly, one or more substituents comprising negatively charged groups or reactive species that can interact with positively charged moieties on growth factors, differentiation factors, chemotactic factors, adhesion molecules and the like in the concentrated fluid. In an embodiment, the coating agent comprising a nonpolymeric core molecule having attached thereto, directly or indirectly, one or more substituents comprising negatively charged groups or reactive species that can interact with positively charged moieties of one or more growth factors, differentiation factors, chemotactic factors, adhesion molecules, or a combination thereof. In accordance with the invention, reactive species comprise one or more first reactive species adapted to attach the coating to a surface, and one or more second reactive species adapted to initiate polymerization. In embodiments, the polymer layers are coated with biodegradable layers of nanoscale polysaccharides, antimicrobial agents, antifungal agents, biologically active macromolecules, such as proteins, peptides and amino acid analogs, for example, and the like. In other embodiments, the polymer layers are coated with cells, cell agglomerates or cell matrices. The polymer layers and methods for making such polymer layers are known in the art, and are further described in, for example, U.S. Pat. No. 6,514,734, incorporated herein by reference.

In other embodiments, the graft material is coated with a nanofiber or microfiber. The nanofiber or micro fiber comprises one or more growth factors, differentiation factors, chemotactic factors, adhesions molecule, or a combination thereof. The molecules can be attached to the surface of the fiber, such as for example by a functional group or charged moiety, or added to the polymer solution prior to electrospinning. In an embodiment, functional groups are deposited on the growth surface by plasma deposition. Plasma deposition creates local plasmas on the surfaces of the fibers. The treated surface is then reacted with gaseous molecules, such as allylamine and/or allyl alcohol, in a reaction chamber. In another embodiment, functional groups are introduced during manufacturing of the fibers. For example, dodecyl amine, dodecyl aldehyde, dodecyl thiol, or dodecyl alcohol can be added to a polymer solution during the manufacturing process. A portion of the added amines, aldehydes, sulphydryl, or alcohol moieties, respectively, are exposed at the surface of the fiber. Examples of suitable nanofibers and microfibers are described, for example, in U.S. 2005/0059695, WO 2006/094076, U.S. 2007/0082393, and are commercially available, for example, from Surmodics (Minneapolis, Minn.).

Solubility or insolubility of the nanofibers or microfibers can be engineered to control the release the one or more growth factors, differentiation factors, chemotactic factors, adhesions molecule, or combination thereof of bioactive molecules from the nanofibers or microfibers. In an embodiment, the rate of release is determined by the rate of degradation and/or dissolution of the polymer or copolymer comprising the nanofiber or microfiber.

In some embodiments, above void filter, such as demineralized bone matrix (DBM) is reconstituted in and/or coated with a concentrated fluid obtained from a concentrator of the invention. In an embodiment, the fluid is concentrated autologous PRP. The concentrator can used to obtain concentrated PRP from a sample of patient blood during surgery. The concentrated PRP can be mixed with a bone void filler, such as DBM. Suitable DBMs can be obtained from LifeNet of Virginia Beach, Va., under the names CELLECT, CEL25, DCAN5 (Demineralized Cancellous 1-4 mm), DGC20 or DGC 40 (Demineralized Cortical Bone), GDS005 GDS 010 or GDS015 (I/C Graft Chambers), OPTIUM Gel AGEL05 or AGEL10 (for non-weight bearing applications), OPTIUM Putty APUT05 or APUT05 (for non-weight bearing applications), and from Osteotech, Inc. of Eatontown, N.J., under the names GRAFTON DBM CRUNCH and GRAFTON DBM MATRIX PLF. The DBMs can be freeze dried for subsequent use for mixing with the concentrated platelet rich plasma during surgery. Once mixed with the bone void filler, such as DBM, the resultant mixture is applied during surgery in any of numerous applications, including, without limitation, spinal fusion, spinal defects, trauma, bone cysts, bone tumors, fracture management, filling of osseous defects, augmenting total joints, sinus augmentation, ridge preservation, joint revisions, posterolateral fusion procedures and general orthopedics applications. Mixing the patient's own concentrated PRP with bone void filler for surgical application back into the patient results in increased osteoconductivity and faster bone growth. The bone void filler material is more likely to be readily accepted by the patient's immune system and a lower chance of rejection, and aids in regeneration of bone tissue around the bone void filler material.

Tissue Regeneration/Culture Methods

Concentrated fluids obtained by the methods of the invention can be used in tissue regeneration, tissue culture, and cell culture. Concentrated fluids comprising one or more growth factors, differentiation factors, chemotactic factors, adhesions molecule, or a combination thereof can be added to a growth matrix or added directly to tissue or cell culture media. In an embodiment, the concentrated fluid is applied to the site of a wound or injury in order to promote proliferation of cells and repair and regeneration of tissue in the wound site.

The filter housing of a concentrator of the invention can be configured as a growth chamber. In such an embodiment, the filter housing is fitted with a growth matrix or growth surface. Examples a growth matrix or growth surface include but are not limited to a network of one or more nanofibers, a nanofibrillar structure, glass, silicon or plastic comprising an etched or micropatterned surface, glass, silicon or plastic surface comprising macropores or nanopores, a polymer scaffold, a woven scaffold, a woven or net textile, an extruded scaffold, a rod, a screw, a wire, a mesh, or a cage. In some embodiments, the growth matrix or growth surface can be glass, polymeric, metallic, ceramic, cellulosic, or proteinaceous. In some embodiments, a surface of the growth matrix is coated with nanofibers or a polymeric coating that supports the growth and/or attachment of cells seeded on or to the surface. An example of a suitable surface includes, but is not limited to, a surface of a rod, screw, wire, mesh, or cage. Examples of nanofibers and/or polymeric coatings that support the growth and/or attachment of cells to or on a coated surface are described herein and are known in the art.

In an embodiment, the growth matrix is a nanofibrillar structure. The nanofibrillar structure can be layered to form a multi-layered nanofibrillar assembly. A diverse array of growth environments for a cell or tissue can be constructed by engineering specific chemical and physical properties into the nanofiber network, substrate, and/or spacers comprising the individual nanofibrillar structure and/or sequentially layering individual nanofibrillar structures.

Specific nano- and/or micro-environments can be engineered within individual nanofibrillar structures or within an assembly comprising two or more layered nanofibrillar structures. Physical properties and/or characteristics of individual nanofibrillar structures including, but not limited to, surface roughness, adhesivity, porosity, solidity, elasticity, geometry, interconnectivity, surface to volume ratio, fiber diameter, fiber solubility/insolubility, hydrophilicity/hydrophobicity, fibril density, and fiber orientation can be engineered to mimic the nanotopography of ECM or BM. For example, the physical and geometric properties of the nanotopography of the individual nanofibrillar structures of the assembly can be engineered to mimic the nanotopography of the extracellular matrix or basement membrane.

Specific recognition motifs such as peptides, polypeptides, lipids, carbohydrates, amino acids, nucleotides, nucleic acids, polynucleotides, or polysaccharides including, but not limited to, growth factors, differentiation factors, fibrous proteins, adhesive proteins, glycoproteins, functional groups, adhesive compounds, and targeting molecules can be engineered into the nanofibrillar network, substrate, and/or spacers of the individual nanofibrillar structures or multi-layered assembly either isotropically or as gradients to promote appropriate cellular activity, including cell growth and/or differentiation. Embodiments involving amino acids, peptides, polypeptides, and proteins can include any type of such molecules of any size and complexity as well as combinations of such molecules. Examples include, but are not limited to, structural proteins, enzymes, growth factors, differentiation factors, and peptide hormones.

Nanofibrillar growth matrices and methods of using growth matrices for cell proliferation and differentiation and culturing cells or tissue are described in detail, for example, in U.S. 2005/0095695 and WO 2006/094076, incorporated herein by reference.

In an embodiment, a fluid, cells, or tissue is added to the separation chamber of a concentrator of the invention and the concentrator is centrifuged or separated by gravitational weight. In an embodiment, the tissue is disrupted tissue. In an embodiment, the fluid, cells, or tissue are autologous. A desired cellular fraction is removed from the separation chamber and transferred via the transfer ports to the filter chamber comprising a growth matrix. The cells can be cultured on the growth matrix within the concentrator or the growth matrix can be removed and cultured separately. Cells or tissue can be grown on the growth matrix in vivo, in vitro, or ex vivo using known methods and conditions. Cells useful in the methods of the invention include stem cells, somatic cells, committed stem cells, differentiated cells, and tumor cells. The cells can be from a mammal. The mammal can be human. The cells can be a tissue. Examples of tissue include skin, bone, liver, heart, kidney, bladder, muscle, ligament, tendon, cartilage, brain, retina, cornea, and pancreas. Examples of cells useful in the methods of the invention include, but are not limited to, osteoblasts, myoblasts, neurons, fibroblasts, glioblasts, germ cells, stem cells, hepatocytes, chondrocytes, keratinocytes, smooth muscle cells, cardiac muscle cells, connective tissue cells, glial cells, epithelial cells, endothelial cells, hormone-secreting cells, neurons, and lymphoid cells such as B cells, T cells, macrophages, and neutrophils. Examples of stem cells include, but are not limited to, embryonic stem cells, mesenchymal stem cells, bone marrow stem cells, and umbilical cord stem cells. The stem cells can be mammalian stem cells. In an embodiment, the stem cells are human. In an embodiment, the stem cells are embryonic stem cells.

The cells can be from the recipient, a nonspecific donor from the same species, or a donor from a different species. The cells can be from the tissue of a transgenic animal wherein the cell has been engineered to express one or more polynucleotides, repress the expression of one or more polynucleotides, or both. An example of genetically engineered cells useful in the methods of the present invention is cells engineered to make and secrete one or more desired bioactive molecules. When these cells are implanted in an organism or patient, the bioactive molecules produced by the cells can produce a local effect or a systemic effect. Examples of bioactive molecules include growth factors, differentiation factors, and hormones. Examples of hormones include insulin, human growth factor, erythropoietin, thyroid stimulating hormone, estrogen, or progesterone. Cells can be engineered to produce an antigen. These cells can be implanted into an organism or patient to produce an immune response. Cells can be engineered to produce bioactive molecules that inhibit or stimulate inflammation, facilitate healing, resist immuno-rejection, provide hormone replacement, replace neurotransmitters, inhibit or destroy cancer cells, promote cell growth, inhibit or stimulate formation of blood vessels, augment tissue, and promote or induce supplementation or replacement of skin, synovial fluid, tendons, cartilage, ligaments, bone, muscle, organs, dura, blood vessels, bone marrow, and extracellular matrix.

Genetic engineering can involve, for example, adding or removing genetic material to or from a cell, altering existing genetic material, or both using standard recombinant methods. Embodiments in which cells are transfected or otherwise engineered to express a polynucleotide can use transiently or permanently transfected polynucleotide, or both. Polynucleotide sequences can be full or partial length, cloned or naturally occurring.

Stem Cell Methods

In some embodiments, the concentrated fluid of the invention is a fluid comprising bone marrow-derived stem cells. In an embodiment, the concentrated fluid is autologous. In an embodiment, a surgeon inserts a large needle directly into the bone marrow cavity of bones of the lower back, of a patient and aspirates bone marrow out of the bones by inserting the needle into the bone multiple times. The aspirated bone marrow is then centrifuged in a concentrator of the invention, such as at 400 g for 5 minutes. The aspirated bone marrow is a blood-like substance with sufficiently different cell and molecule sizes and weights that the centrifuging process induces separation of the bone marrow into different fractions. If desired, prior to centrifuging the aspirated bone marrow can be mixed with 0.56% (0.075 M) KCl (0.56 g in 100 ml deionized water). The bottom layer is then removed and filtered at 1 to 10 and preferably 4 passes through the filter. The layers are filtered using a filtration system comprising a filter element or membrane as described elsewhere in this Application.

In some embodiments, the concentrated fluid is a fluid comprising cord blood-derived stem cells. In an embodiment, blood is obtained from an umbilical cord during birth. The cord blood can be centrifuged in a concentrator of the invention, such as at 400 g for 5 minutes, thereby inducing separation of the cord blood into different fractions. The bottom layer is removed and filtered at 1 to 10 and preferably 4 passes through the filter, thereby obtaining a substance with an increased concentration of cord blood derived stem cells. The layers are filtered using a filtration system comprising a filter element or membrane as described elsewhere in this Application.

The collection window of the device is infinitely adjustable along the column of the centrifuged body fluid, allowing more accurate collection of the concentrated autologous bone-marrow-derived stem cells. The fluid collected with the stem cells can be used for binding the cells and chips bone material. The fluid collected with the stem cells also helps maintaining the viability of the stem cells for a longer period of time by maintaining a consistent environment for the stem cells.

The resulting concentrated stem cells are then injected or applied within a patient at a particular location of interest. In some embodiment, the stem cells are injected or administered with a carrier, such as DBM. For example, concentrated stem cells can be injected into the brain as a treatment for brain damage or into or adjacent the spinal cord after a spinal cord injury or disease such as ALS (Lou Gehrig's disease). The concentrated stem cells can be injected into a muscle which has undergone muscle damage, particularly into the heart such as for the treatment of non-ischemic (idiopathic) and ischemic heart failure. The stem cells can be injected into the circulatory system or back into the bone marrow to increase red blood cell production. The concentrated stem cells can be placed into the gums to form tooth buds, can be placed into the cochlea to induce cochlear hair cell regrowth as a treatment for deafness, or can be transplanted over a damaged retina as a treatment for blindness. The concentrated stem cells can be topically applied to treat a soft tissue wound or burn or similar injury. The concentrated stem cells can be added to an injured or fractured bone to facilitate bone healing. The concentrated stem cells can also be used for diagnosis purposes.

Sperm Selection and Separation

A concentrator and methods of the invention can be used for sperm selection. In an embodiment, the concentrator device can be used to collect sperm and select either X- or Y-genotype sperm from a sample of mammalian seminal fluid. These methods are predicated on the fact that the two sperm genotypes of mammals (X and Y) may be separated according to pH or density characteristics. In an embodiment, the sperm is obtained from a livestock mammal, such as a bovine, horse, pig, sheep, or goat. For separation by density characteristics, application of buoyant forces within a liquid separation medium causes more buoyant sperm to obtain a different level in the separation medium than less buoyant sperm. When a sample of seminal fluid is centrifuged using the device of the invention, the fluid is separated into fractions containing either the X or the Y-genotype sperm because of the difference in density of each genotype. When the sample of seminal fluid is a sample from a human patient, separation into X and Y-genotype sperm requires the application of a pH gradient in the concentrator of the invention. Substantially pure sperm fractions (having either X or Y-genotype characteristics) are isolated as either the top layer or the bottom layer of the concentrated fluid obtained from the device of the invention. Under certain circumstances, separation of the sperm into fractions or concentration in one particular genotype is enhanced by the application of pressure (positive or negative) to the filtration element or filter membrane of the device. Methods for density separation of sperm are known and described, for example, in U.S. Pat. No. 4,327,177, incorporated herein by reference.

Protein Selection and Separation

The concentrator and methods of the invention can used for protein selection or separation. In an embodiment, the proteins can be growth factors, differentiation factors, chemotactic factors, or adhesion molecules. Proteins from the following general classes can also be used with the methods of the invention: prealbumins (thyroxine- and retinol-binding proteins), albumins, $\alpha$- and $\beta$-globulins, apolipoproteins, coagulation proteins, cell-related plasma proteins, immunoglobulins, amyloid proteins and the like. These protein families and individual proteins, derived from Frank Putnam "The Plasma Proteins", Volume IV, 2nd Edition, 1984, are provided in Table I.

TABLE I

Plasma Proteins

| | Species | Subunit Structure | Chain Length | Protein MW |
|---|---|---|---|---|
| Prealbumin, thyroxine-binding | | | | |
| Protein | Human | Noncovalent tetramer of identical chains | 127 | 54,980 |
| Prealbumin, thyroxine-binding Retinol-binding protein | | | | |
| Protein Retinol-binding protein Albumin | Human | Single chain | 182 | 20,957 |
| Protein Albumin | Human | Single chain | 585 | 66,458 |
| | | Nucleic acid precursor | 609 | 69,365 |
| | Bovine | Single chain | 582 | 66,210 |
| | | Nucleic acid precursor | 606 | |
| | Porcine | Single chain | ~575 | ~66,300 |
| | Ovine | Single chain | 575 | ~66,300 |
| | Chicken | Single chain | 575 | ~66,300 |
| | Rat | Single chain | 584 | 64,600 |
| | | Nucleic acid precursor | 608 | |
| $\alpha$-Globulins Protein | | | | |
| $\alpha$-Globulins | Human | Single chain | 167 | 26,000 |
| $\alpha_1$-Microglobulin | Human | Single chain | 181 | 40,000 |
| $\alpha_1$-Acid glycoprotein | Rat | Nucleic acid precursor | 187 | ~40,000 |
| $\alpha_1$-Antitrypsin | Human | Single chain Nucleic acid precursor | 394 | 54,000 |
| | Baboon | Nucleic acid precursor | 394 | ~54,000 |
| $\alpha_1$-Antichymortrypsin | Human | Single chain | ~440 408 | 68,000 |
| $\alpha_2$-Antiplasmin | Human | Single chain | | 65,000 |
| $\alpha_1$-Fetoprotein | Human | Nucleic acid precursor | 590 | 66,300 |
| | Rat | Nucleic acid precursor | | |
| | Mouse | Nucleic acid precursor | 586 | 72,000 |
| 9.5 S $\alpha_1$-Glycoprotein | Human | Two pentagons (10 non-covalently bound identical subunits) | $(182)_{10}$ | ~250,000 |

TABLE I-continued

Plasma Proteins

| | Species | Subunit Structure | Chain Length | Protein MW |
|---|---|---|---|---|
| (serum amyloid P component) | Human | Possibly a single chain | ~480 | 68,000 |
| $\alpha_1$B-Glycoprotein | Human | Single chain | ~776 | 85,000 |
| $\alpha_1$T-Glycoprotein | Human | Single chain | ~450 | 52,000 |
| Vitamin D-binding protein (Gc globulin) | Human | Single chain | | 54,000 |
| Thyroxine-binding protein | Human | Single chain | | ~160,000 |
| Inter-α-trypsin inhibitor | Human | Single chain (easily cleaved) | 1,046 | 132,000 |
| Ceruloplasmin | Human | Single chain | ~440 | ~58,500 |
| 3.8 S Histidine-rich $\alpha_2$-glycoprotein | Human | Single chain | ~213 | 81,000 |
| Galactoglycoprotein | Human | Single chaine | 312 | 50,000 |
| 3.1 S Leucine-rich $\alpha_2$-glycoprotein | Rat (male) | Nucleic acid precursor | 162 | 18,709 |
| $\alpha_2\mu$-Globulin | Human | Single chain | ~258 | 41,000 |
| Zn-$\alpha_2$-Glycoprotein | Human | Two chains (A & B) | ~359 | 49,000 |
| $\alpha_2$HS-Glycoprotein | | B chain | 27 | 3,386 |
| | Human | 4 identical subunits | 1,450 | 725,000 |
| $\alpha_2$-macroglobulin | Human | Single chain | ~465 | 60,000 |
| 4S-$\alpha_2,\beta_1$-Glycoprotein | Human | 2 pairs of nonidentical chains $(\alpha\beta)_2$ | 656 | 86,018 |
| Haptoglobin | | Single-chain precursor | 245 | |
| | | $\alpha^1$ chain | 83 | 9,189 |
| | | $\alpha^2$ chain | 142 | 15,939 |
| | | β chain | 245 | 33,820 |
| | | β chain | | |
| | Canine | One pair of chains (αβ) β chain | | |
| | Human | Single chain | | 52,000 |
| Corticosteroid-binding globulin | Human | Tetramer | | 220,000 |
| 8 S $\alpha_3$-Glycoprotein | | | | |
| β-Globulins | | | | |
| Protein | | A trimeric aggregate | $(42,300)_n$ | |
| Pregnancy-specific $\beta_1$-glycoprotein | Human | Single chain | 678 | 79,550 |
| Human Transferrin | | | 679 | |
| | Chicken | Single chain | 686 | 77,770 |
| Ovotransferrin | | Nucleic acid precursor | 686 | |
| | Human | Single chain | 439 | 60,000 |
| Hemopexin | Rabbit | Single chain | ~440 | 57,000 |
| | Human | Single chain | 99 | 11,731 |
| $\beta_2$-Microglobulin | Mouse | Single chain | 99 | |
| | Rabbit | Single chain | 99 | |
| | Guinea pig | Single chain | 99 | |
| | Human | Subunits aggregate as cyclic pentamers | 187 | $(20,946)_5$ |
| C-Reactive protein | Rabbit | Pentagonal structure | 186 | |
| | Human | Single chain | 326 | ~50,000 |
| $\beta_2$-Glycoprotein I | Human | Single chain, forms complex | | 35,000 |
| $\beta_2$-Glycoprotein III | | | | |
| Apolipoproteins | | | | |
| Protein | Human | Single chain; no disulfides | 243 | 28,076 |

TABLE I-continued

Plasma Proteins

| | Species | Subunit Structure | Chain Length | Protein MW |
|---|---|---|---|---|
| Apolipoprotein A-I (HDL) | Human | Dimer of 2 identical chains, joined by disulfide | 77 | 17,414 |
| Apolipoprotein A-II (HDL) | Human | Single chain; no disulfides | 57 | 6,631 |
| Apolipoprotein C-I (VLDL) | Human | Single chain; no disulfides | 78 | 8,829 |
| Apolipoprotein C-II | Human | Single chain glycopeptide | 79 | 8,764 |
| Apolipoprotein C-III (VLDL) | Human | Single chain | 299 | 34,183 |
| Apolipoprotein E γ-Mobility (non-immunoglobulin) | | | | |
| Protein | Human | Single chain | 47 | 5,100 |
| 0.6 S γ₂-Globulin | Human | Single chain | 132 | 14,000 |
| 2 S γ₂-Globulin | Human | Single chain | ~85 | 9,000 |
| Basic Protein B2 | Human | Single chain | 120 | 13,248 |
| Post-γ-Globulin (γ-trace) Complement Components | | | | |
| Protein | Human | Six identical nocovalently-linked subunits, each with three similar chains (A, B & C) Total of 18 chains | | 410,000 |
| C1q | | B chain | 226 | |
| | | C chain | ~200 | |
| | Human | Noncovalent dimer | | (83,000)₂ |
| C1r | Human | B chain | 242 | 27,096 |
| C1r | Human | Single chain | | 83,000 |
| C1s | Human | Two chains (a and b) | | 83,000 |
| C1s | Human | Single chain | | 102,000 |
| C2 | Human | Two disulfide-bonded chains | ~1,630 | ~185,000 |
| C3 | | α chain | ~960 | 115,000 |
| | | β chain | ~670 | 75,000 |
| | Mouse | ProcC3 is a single-chain precursor | | ~190,000 |
| | Human | Fragment of C3 α chain | 77 | 9,093 |
| C3a | Porcine | Fragment of C3 α chain | 77 | ~9,000 |
| | Rat | Fragment of C3 α chain | 78 | ~9,000 |
| | Mouse | Fragment of C3 α chain | 78 | ~9,800 |
| | Human | Three disulfide-bonded chains | | |
| C4 | | α chain | ~785 | 93,000 |
| | | β chain | ~660 | 75,000 |
| | | γ chain | ~250 | 33,000 |
| | Human | Fragment of a chain | 77 | 8,763 |
| C4a | Bovine | Fragment of a chain | 77 | |
| | Human | Two disulfide-bonded chains | | 185,000 |

TABLE I-continued

Plasma Proteins

| | Species | Subunit Structure | Chain Length | Protein MW |
|---|---|---|---|---|
| C5 | | α chain | ~960 | 115,000 |
| | | β chain | ~670 | 75,000 |
| | Human | Fragment of α chain | 74 | 8,274 |
| C5a | Human | Single chain | ~900 | 1,048,000 |
| C6 | Human | Single chain | ~800 | 92,400 |
| C7 | Human | Two noncovalently-linked subunits | | 163,000 |
| C8 | Human | Disulfide-bonded subunits (Mr 75,000) | | 540,000 |
| C4-Binding Protein | Human | Single chain | | 24,000 |
| Factor D (C3 Proactivator Convertase) | Human | Single chain | | 90,000 |
| Factor B (C3 Proactivator) | | Bb Fragment | 505 | 60,000 |
| | Human | Four non-covalent identical chains | ~480 | 220,000 |
| Properdin | Human | Single chain | ~1,275 | 155,000 |
| Factor H ($\beta_1$H) | Human | Two disulfide-bonded chains | | 90,000 |
| C3b-Inactivator | | Light chain | | 40,000 |
| | | Heavy chain | | 50,000 |
| Coagulation Proteins | | | | |
| Protein | Human | Single chain | 581 | 72,000 |
| Prothrombin | Bovine | Single chain | 582 | 72,000 |
| | Bovine | Two disulfide-linked chains | ~340 | 37,000 |
| Thrombin | | A chain | 49 | 5,728 |
| | | B chain | 259 | 31,000 |
| | Human | Single chain (two chains when activated) | | 48,000 |
| FactorVII | Human | Noncovalent complex | | (100,000)n |
| Factor VIII | Human | Single chain Precursor | 462 | 51,801 |
| Factor IX | Bovine | Single chain | 427 | ~55,000 |
| | Human | Heavy and light chains | 381 | |
| Factor IXa (activated) | | Light chain | 145 | |
| | | Heavy chain | 236 | |
| | Bovine | Heavy and light chains | 390 | ~46,500 |
| | | Light chain | 146 | 16,600 |
| | | Heavy chain | 232 | 27,300 |
| | Human | Heavy and light chains | | 59,000 |
| Factor X | | Light chain | 139 | 16,211 |
| | Bovine | Heavy and light chains | 447 | 55,000 |
| | | Light chain | 140 | 16,143 |
| | | Heavy chain | 307 | 38,000 |
| | Bovine | Heavy and light chains | 396 | 44,000 |
| Factor Xa Activated | | Light chain | 140 | 16,000 |
| | | Heavy chain | 256 | 28,000 |
| | Human | Two identical disulfide-linked chains | | 130,000 |
| Factor XI | Bovine | Two disulfide-linked chains | 415 | 55,000 |

TABLE I-continued

Plasma Proteins

| | Species | Subunit Structure | Chain Length | Protein MW |
|---|---|---|---|---|
| Protein C | | Light chain | 155 | 21,000 |
| | | Heavy chain | 260 | 35,000 |
| | Human | Single chain | | ~69,000 |
| Protein S | Bovine | | | ~66,000 |
| | Bovine | Single chain | | ~50,000 |
| Protein Z | Human | Three pairs of disulfide bonded chains | 2,964 | 340,000 |
| Fibrinogen | | α chain | 610 | 64,115 |
| | | β chain | 461 | 52,314 |
| | | γ chain | 411 | 46,468 |
| | Human | Single chain | 790 | ~92,000 |
| Plasminogen | | Two-chain after activation | 790 | |
| Plasmin | | Heavy chain (A) | 560 | |
| | | Light chain (B) | 230 | |
| | Human | Single chain | | 76,000 |
| Factor XII | | Two pairs of non-identical chains (a2b2) | | 320,000 |
| Factor XIII (Transglutaminase) | Bovine | Single chain Precursor | 621 | |
| HMW and LMW Prekininogens | Bovine | Heavy chain | 361 | |
| LMW Kininogen | | Light chain | 47 | |
| | Human | Single chain | 430 | 58,000 |
| Antithrombin III | | | | |
| Cell-Related Plasma Proteins | | | | |
| Protein | Human | Disulfide-linked Dimer | ~1,900 | ~440,000 |
| Fibronectin | Human | Disulfide-linked Dimer | ~1,880 | ~440,000 |
| | Human | Tetramer of identical chains | 81 | 35,404 |
| β-Thromboglobulin | Human | Tetramer of identical chains | 70 | (7,769)$_4$ |
| Platelet Factor-4 | Bovine | Single chain | 60 | 6,647 |
| Serum Basic Protease Inhibitor | | | | |
| Immunoglobulins (Antibodies) | | | | |
| Protein | Higher Vertebrates | Four disulfide-bonded chains, two heavy and two light | | (160,000)$_n$ |
| Immunoglobulins (Antibodies) | Human | Monomer of dimer | ~214 | ~23,000 |
| κ or λ Light Chains (Bence Jones Proteins) | Human | Kappa (κ) | ~214 | ~23,500 |
| | | Lambda (λ) | ~214 | ~23,000 |
| | Human | (γκ)$_2$ or (γλ)$_2$ monomer | | ~150,000 |
| Immunoglobulin G (IgG) | | γ1 Heavy chain | ~475 | ~50,000 |
| IgG$_1$ | | γ2 Heavy chain | ~450 | ~50,000 |
| IgG$_2$ | | γ3 Heavy chain | ~475 | ~55,000 |
| IgG$_3$ | | γ4 Heavy chain | ~450 | ~50,000 |
| IgG$_4$ | Human | (α$_2$κ$_2$)$_n$ or (α$_2$λ$_2$)$_n$ n = 1, 2 or 4 | | ~(160,000)n |
| Immunoglobulin A (IgA) | | α1 Heavy chain | ~475 | ~60,000 |

TABLE I-continued

Plasma Proteins

| | Species | Subunit Structure | Chain Length | Protein MW |
|---|---|---|---|---|
| IgA1 | | $\alpha 2$ Heavy chain | ~450 | ~60,000 |
| IgA2 | Human | $\mu_2\kappa_2$ or $\mu_2\lambda_2$ monomer | | ~950,000 |
| Immunoglobulin M (IgM) | | $\mu$ Heavy chain | ~575 | ~75,000 |
| | Human | $\delta_2\kappa_2$ or $\delta_2\lambda_2$ monomer | ~510 | ~175,000 |
| Immunoglobulin D (IgE) | | $\delta$ Heavy chain | | ~65,000 |
| | Human | $\sigma_2\kappa_2$ or $\sigma_2\lambda_2$ monomer | | ~190,000 |
| Immunoglobulin E (IgE) | | $\sigma$ Heavy chain | ~550 | ~72,000 |
| | Human | Single chain | 129 | 14,619 |
| J Chain | | Single chain Precursor | 137 | |
| Amyloid Proteins (Non-Immunoglobulin) | | | | |
| Protein | Human | Single chain Precursor | 104 | 11,683 |
| Amyloid-Related Apoprotein (apoSAA$_1$) | Human | Single chain Precursor | 76 | 9,150 |
| AA (FMF) (ASF) | Human | Single chain Precursor | 76 | 9,145 |
| AA (TH) (AS) | Human | Ten Subunits aggregates as two pentamers | ~184 | ~25,000 |
| Serum Amyloid P Component (9.5 S 7$\alpha$1-glycoprotein) Misc. Trace Components | | | | |
| Protein | Human | AA | | |
| Carcinoembryonic Antigen | Human | AA | | Asp |
| Angiotensinogen | Rat | Single chain Precursor NA | 49,548 | Asp |

The basic methodology for protein selection and collection involves centrifuging or other gravity separation of a biological fluid or disrupted cells or tissue. The height or window of the column which contains the specific desired protein can be infinitely adjusted to select the desired protein and collect the fluid. As discussed herein, various filters can be used to further hone the concentration or concentrate specific proteins. This method of selection and collection helps to maintain protein viability and activity by maintaining their environment in the natural fluid.

The proteins can be used, for example, for healing, surgical applications, therapeutic applications, tissue or cell culture, diagnostic purposes, or reapplied into a patient's body. In an embodiment, one of more growth factors, one or more differentiation factors, one or more chemotactic factors, one or more adhesion molecules, or a combination thereof is administered to bone, cartilage, a wound, soft tissue injury, or surgical site to promote healing. The concentrated proteins can also be mixed with stem cells. The cartilage can be wounded, damaged, or severed. The wound can be a surgical incision, abrasion, ulcer, burn, or any other break in the skin. In an embodiment, one or more growth factors, one or more differentiation factors, one or more chemotactic factors, one or more adhesion molecules, or a combination thereof is administered to a subject to treat an orthopedic disorder or during or after a surgical procedure to correct an orthopedic disorder to promote healing. The concentrated proteins can also be administered with stem cells. In an embodiment, the concentrated proteins and/or stem cells are administered to the surgical site. In an embodiment, the orthopedic disorder comprises spinal fusion, spinal defect, bone trauma, bone cyst, bone tumor, bone fracture, filling of osseous defect, joint augmentation, sinus augmentation, ridge preservation, joint revision, or posterolateral fusion.

In an embodiment, fluid or tissue from the kidney can be autologously concentrated in a device of the invention to obtain concentrated specimens of or fractions containing erythropoietin, urodilatin, calcitrol, and/or rennin Fluid or tissue from the spleen can be autologously concentrated to obtain concentrated specimens of or fractions containing opsonins, properdin, and tuftsin. Fluid or tissue from the liver can be autologously concentrated to obtain concentrated specimens of or fractions containing bile, hepatocytes, cholangiocytes, unipotential or bipotential stem cells, insulin-like growth factor (IGF); angiotensinogen, and/or thrombopoietin. Fluid or tissue from the thyroid can be autologously concentrated to obtain concentrated specimens of or fractions containing hormones, principally thyroxine ($T_4$), triiodothyronine ($T_3$) and/or calcitonin. Fluid or tissue from the hypothalamus can be autologously concentrated to obtain concentrated specimens of or fractions containing corticotropin-releasing hormone (CRH), dopamine, gonadotropin-releasing hormone (GnRH), growth hormone releasing hormone (GHRH), somatostatin thyrotropin-releasing hormone (TRH), and/or hypocretin. Fluid or tissue from the pineal gland can be autologously concentrated to obtain concentrated specimens of or fractions containing melatonin. Fluid or tissue from the pituitary gland can be autologously concentrated to obtain concentrated specimens of or fractions containing TRH (thyrotropin-releasing hormone), CRH (corticotropin-releasing hormone), DA (dopamine, "prolactin inhibiting factor"/PIF), GnRH (gonadotropin-releasing hormone), GHRH (growth hormone releasing hormone), prolactin, follicle-stimulating hormone, luteinizing hormone, thyroid-stimulating hormone, adrenocorticotropic hormone, endorphins and/or growth hormones. Fluid or tissue from the parathyroid can be autologously concentrated to obtain concentrated specimens of or fractions containing Parathyroid hormone (PTH). Fluid or tissue from the heart can be autologously concentrated to obtain concentrated specimens of or fractions containing atrial natriuretic peptide. Fluid or tissue from the stomach and/or intestines can be autologously concentrated to obtain concentrated specimens of or fractions containing cholecystokinin (CCK), gastrin, ghrelin, neuropeptide, secretin and/or somatostatin. Fluid or tissue from the pancreas can be autologously concentrated to obtain concentrated specimens of or fractions containing insulin, glucagons, somatostatin, pancreatic polypeptide, paracrine, autocrine and/or other hormones produced in the Islets of Langerhans. Fluid or tissue from the adrenal glands can be autologously concentrated to obtain concentrated specimens of or fractions containing glucocorticoids (Cortisol), mineralocorticoids (aldosternone), and/or androgens (DHEA & testosterone). Fluid or tissue from the testes can be autologously concentrated to obtain concentrated specimens of or fractions containing androgens and/or testosterone. Fluid or tissue from the ovary can be autologously concentrated to obtain concentrated specimens of or fractions estrogens (estradiol) and/or progesterone. Fluid or tissue from the placenta can be autologously concentrated to obtain concentrated specimens of or fractions containing progesterone, estrogens, human chorionic gonadotropin, and/or human placental lactogen. Fluid or tissue from the thalamus or other portions of the endocrine system can be similarly autologously concentrated.

DNA Purification Methods

The concentrator and methods of the invention can be used for isolation and purification of DNA. In embodiments, the DNA can be genomic DNA, plasmid DNA, DNA isolated from tissues or cells, synthetic oligonucleotides, and the like. The basic methodology for DNA isolation and purification involves disrupting the DNA-containing cells or tissue by chemical or mechanical means. The disrupted cells or tissue are then filtered using the filter element and then centrifuged in the concentrator of the invention. The cell or tissue layer is retained on the filter element, while the application of pressure allows the DNA-containing fluid layer to pass through the filter and into the centrifuge chamber of the concentrator device. Centrifugation can be performed on the ultracentrifuge or microcentrifuge scale, at high speeds of up to 15,000 RPM. Various filters can be used to further hone the purification of DNA using the concentrator of the invention. For example, the filter element of the invention can be an affinity column on which DNA in a fluid is preferentially adsorbed and then eluted. The methods of the invention allow DNA to be purified in a simple and efficient manner, with minimal mechanical or chemical manipulation. Purified DNA obtained by the methods of the invention can be used for a variety of diagnostic and therapeutic purposes.

Other Uses and Applications

In some embodiment, a concentrated fluid, such as PRP and/or PPP, can be applied to a hemostasis gauze or pad. The gauze or pad may be formed of a woven gauze material or a non-woven bandage material. The gauze or pad is preferably formed of a bioabsorbable material. Alternative, a non-woven bandage material may be filled with autologous concentrated PRP. In an embodiment, the hemostasis gauze or pad is applied to a wound site. The hemostasis gauze or pad can be directly applied to a site of bleeding to initially stop the bleeding, such as a vascular access sites after removal of a percutaneous catheter or tube, and then to accelerate tissue healing as the gauze or pad is bioabsorbed.

In an embodiment, the hemostasis gauze or pad can be coated with or contain other known hemostasis agents. For example, concentrated PRP and/or PPP may be applied to a CHITO-SEAL topical hemostasis pad available from Abbott Vascular of Santa Clara, Calif., which is a soft, sterile, non-woven pad coated with chitosan. Chitosan is produced commercially by deacetylation of chitin (can be produced from chitin also), which is the structural element in the exoskeleton of crustaceans (crabs, shrimp, etc.). The concentrated PRP and/or PPP may also be applied to a pad containing thrombin separated from bovine plasma to enhance the hemostasis properties of the pad. Commercially available examples of thrombin-containing pads are available from Vascular Solutions of Minneapolis, Minn. as D-STAT DRY, D-STAT RADIAL, THROMBIGEL, D-STAT 2DRY and THROMBIX.

Concentrated PRP and/or PPP obtained as described above can be used in flow hemostasis. The concentrated PRP or PPP can be autologous. Concentrated PRP and/or PPP can be applied directly in liquid form to the surface of a wound site. The concentrated PRP and/or PPP aids in inhibiting active bleeding from the wound by initiating the body's own clotting mechanisms. In an embodiment, autologous concentrated PRP and/or PPP is combined with other pre-sourced procoagulent components, such as collagen and thrombin. The concentrated PRP and/or PPP can be used to stop any active surface bleeding, and is particularly useful for direct application to radial artery access sites, to dialysis graft punctures following de-clotting procedures, to PICC/in-dwelling intravenous lines, and following arterial and venous sheath removal.

Concentrated PPP obtained as described above can be applied directly in liquid form to the surface of a wound site. The autologous concentrated PPP helps to stop active bleeding from the wound by initiating the body's own clotting mechanisms. If desired, the autologous concentrated PPP may be combined with other presourced procoagulent components such as collagen and thrombin. The autologous concentrated PPP can be used to stop any active surface bleeding, and is particularly considered for direct application to radial artery access sites, to dialysis graft punctures following de-clotting procedures, to PICC/in-dwelling intravenous lines, and following arterial and venous sheath removal.

In some embodiments, the concentrated fluid of the invention is a combination of PRP and PPP. The concentrated fluid can be autologous. In an embodiment, a concentrator of the invention is used to obtain concentrated platelet rich and concentrated platelet poor plasma from a sample of patient blood during surgery. Whole blood is withdrawn from the patient, and centrifuged in the '142 concentrator for 5 to 30 minutes at 25 to 10000 g, and most preferably for about 15 minutes at 4000 g. The central layers of platelet rich plasma and platelet poor plasma of the centrifuged blood are visually identified by color and withdrawn from the centrifuge chamber. Both layers are simultaneously passed through the filter unit under syringe pressure for one to ten passes, and most preferably 6 passes. The filtration can be tangential flow or dead end. In an embodiment, tangential flow filtration using hollow polysulfone filter fiber membranes with a size cutoff of 0.1 nm to 100,000 nm and a surface area of 1 cm squared to 6000 cm squared is utilized. The filtration results in concentrated platelet rich/platelet poor plasma ("PRP+PPP"). The concentrated PRP+PPP obtained is a viscous liquid having increased concentrations of platelets, white blood cells, fibrinogen, thrombin, clotting factors and associated proteins and structures as compared to whole blood. Various known diluents, such as buffered saline, can be used to adjust the viscosity of the autologous concentrated PRP+PPP for various applications.

The resultant concentrated PRP+PPP product can be applied during surgery directly to a bone which has been fractured or damaged. The concentrated PRP+PPP produces benefits both of reduced bleeding at the fracture site followed by increased bone growth rates.

In some embodiments, the concentrated PRP+PPP is mixed with a bone void fillers, such as demineralized bone matrix ("DBM"). Once mixed with the bone void filler, the resultant mixture is applied during surgery in any of numerous applications, including but not limited to spinal fusion, spinal defects, trauma, bone cysts, bone tumors, fracture management, filling of osseous defects, augmenting total joints, sinus augmentation, ridge preservation, joint revisions, posterolateral fusion procedures and general orthopedics applications. Mixing the patient's own concentrated PRP+PPP with bone void filler for surgical application back into the patient results in reduced bleeding followed by increased osteoconductivity and faster bone growth.

In some embodiments, the concentrated PRP+PPP is applied as a cartilaginous repair material directly to a cartilage defect. If desired, the concentrated PRP+PPP can be mixed with chondrocytes obtained from a different source. In an embodiment, the chondrocytes are isolated by sequential enzymatic digestion of fall-thickness articular cartilage of skeletally mature bovines with pronase and collagenase.

In some embodiments, the concentrated PRP+PPP is applied to an organ or tissue during transplanting, resulting in reduced bleeding followed by better acceptance of the new organ or tissue from the recipient's immune system and a lower chance of rejection.

In some embodiments, concentrated PRP+PPP is used as a surgical glue material. Either by itself or mixed with other surgical glue materials, the resultant concentrated PRP+PPP is used similar to surgical glue to adhere two tissue portions together.

The various embodiments described above are provided by way of illustration only and should not be construed to limit the invention. Those skilled in the art will readily recognize various modifications and changes that may be made to the present invention without following the example embodiments and applications illustrated and described herein, and without departing from the true spirit and scope of the present invention without following the example embodiments and applications illustrated and described herein, and without departing from the true spirit and scope of the present invention, which is set forth in the following claims.

What is claimed is:

1. A method of using a concentrated biological fluid, comprising:
    inserting a fluid into a concentrator, the concentrator comprising:
        a main housing defining a separation chamber for holding blood during centrifugation;
        a filter unit connected to the separation chamber and comprising a filter housing; and
        a growth matrix disposed within the filter housing;
    loading the concentrator into a centrifuge and processing the fluid in the concentrator;
    identifying a platelet rich plasma (PRP) by visually inspecting the processed fluid;
    withdrawing the PRP from the separation chamber of the concentrator;
    passing the PRP through the filter unit by depressing a syringe that is coupled to the concentrator, wherein the passing results in a concentrated PRP.

2. The method of claim 1, further comprising attaching a ligand to a substrate of the growth matrix to bind a growth factor, differentiation factor, chemotactic factor, or adhesion molecule.

3. The method of claim 2, wherein the attaching comprises forming covalent chemical bonds between functional groups on the ligand and reactive groups on the substrate.

4. The method of claim 1, wherein the growth matrix comprises a network of nanofibers.

5. The method of claim 1, wherein the growth matrix comprises a nanofibrillar structure.

6. The method of claim 1, wherein the growth matrix comprises a glass, silicon, or plastic surface comprising an etched or micropatterned surface.

7. The method of claim 1, wherein the growth matrix comprises a glass, silicon, or plastic surface comprising macropores or nanopores.

8. A method of using a concentrated biological fluid, comprising:
    inserting a fluid into a concentrator, the concentrator comprising:
        a main housing defining a separation chamber for holding blood during centrifugation;
        a filter unit connected to the separation chamber and comprising a filter housing; and
        a growth matrix disposed within the filter housing;
    loading the concentrator into a centrifuge and processing the fluid in the concentrator;
    identifying a platelet poor plasma (PPP) by visually inspecting the processed fluid;
    withdrawing the PPP from the separation chamber of the concentrator;
    passing the PPP through the filter unit by depressing a syringe that is coupled to the concentrator, wherein the passing results in a concentrated PPP.

9. The method of claim 8, further comprising cooling the PPP prior to filtering the PPP with the filter unit to accelerate a precipitation separation.

10. The method of claim 8, further comprising attaching a ligand to a substrate of the growth matrix to bind a growth factor, differentiation factor, chemotactic factor, or adhesion molecule.

11. The method of claim 10, wherein the attaching comprises forming covalent chemical bonds between functional groups on the ligand and reactive groups on the substrate.

12. The method of claim 8, wherein the growth matrix comprises a network of nanofibers.

13. The method of claim 8, wherein the growth matrix comprises a nanofibrillar structure.

14. The method of claim 8, wherein the growth matrix comprises a glass, silicon, or plastic surface comprising an etched or micropatterned surface.

15. The method of claim 8, wherein the growth matrix comprises a glass, silicon, or plastic surface comprising macropores or nanopores.

16. The method of claim 8, further comprising mixing the concentrated PPP with a tissue adhesive to form a glue mixture so that when the glue mixture is used additional growth factors and blood proteins are delivered to a healing site.

17. The method of claim 16, wherein the tissue adhesive is fibrin-based and contains a concentrate of fibrinogen and thrombin.

\* \* \* \* \*